United States Patent
Song et al.

(10) Patent No.: US 10,022,360 B2
(45) Date of Patent: Jul. 17, 2018

(54) POLYMERIC NANOPARTICLES AND METHODS OF MAKING AND USING SAME

(71) Applicants: Merck Sharp & Dohme Corp., Rahway, NJ (US); BIND Therapeutics, Inc., Cambridge, MA (US)

(72) Inventors: Young Ho Song, Natick, MA (US); Greg Troiano, Pembrook, MA (US); Hong Wang, Newton, MA (US); Maria Figueiredo, Somerville, MA (US); Michael H. Lam, Cambridge, MA (US); Caroline McGregor, Cranford, NJ (US)

(73) Assignees: Merck Sharp & Dohme Corp., Rahway, NJ (US); Pfizer Inc., New York, NY (US)

( * ) Notice: Subject to any disclaimer, the term of this patent is extended or adjusted under 35 U.S.C. 154(b) by 0 days.

(21) Appl. No.: 15/126,894

(22) PCT Filed: Mar. 12, 2015

(86) PCT No.: PCT/US2015/020086
§ 371 (c)(1),
(2) Date: Sep. 16, 2016

(87) PCT Pub. No.: WO2015/142605
PCT Pub. Date: Sep. 24, 2015

(65) Prior Publication Data
US 2017/0087135 A1    Mar. 30, 2017

Related U.S. Application Data

(60) Provisional application No. 61/954,128, filed on Mar. 17, 2014.

(51) Int. Cl.
*A61K 31/4375* (2006.01)
*A61K 9/51* (2006.01)

(52) U.S. Cl.
CPC ........ *A61K 31/4375* (2013.01); *A61K 9/5123* (2013.01); *A61K 9/5153* (2013.01)

(58) Field of Classification Search
CPC ................................................. A61K 31/4375
See application file for complete search history.

(56) References Cited

U.S. PATENT DOCUMENTS

| | | | |
|---|---|---|---|
| 7,576,209 B2 * | 8/2009 | Kelly, III | C07D 401/04 544/126 |
| 8,420,123 B2 | 4/2013 | Troiano et al. | |
| 2010/0068286 A1 * | 3/2010 | Troiano | A61K 9/10 424/489 |

FOREIGN PATENT DOCUMENTS

| | | |
|---|---|---|
| EP | 1985309 A1 | 12/2005 |
| WO | WO2012166923 A2 | 12/2012 |
| WO | WO2013044219 A1 | 3/2013 |

OTHER PUBLICATIONS

European Search Report, Application No./Pat. No. 15765824.6 - 1114 / 3119395, PCT/US2015020086, dated Feb. 28, 2018, 7 pages.

* cited by examiner

*Primary Examiner* — Noble E Jarrell
*Assistant Examiner* — John S Kenyon
(74) *Attorney, Agent, or Firm* — Yong Zhao; Catherine D. Fitch

(57) ABSTRACT

Described herein are polymeric nanoparticles that comprise 8-[4-(1-aminocyclobutyl)phenyl]-9-phenyl-2H-[1,2,4]-triazolo-[3,4-fJ[1,6]-naphthyridin-3-one (Compound A), or a pharmaceutically acceptable salt thereof, and methods of making and using such nanoparticles. The nanoparticle comprises about 50 to about 99.8 weight percent of a diblock poly(lactic) acid-poly(ethylene)glycol copolymer or a diblock poly(lactic acid-co-glycolic acid)-poly(ethylene) glycol copolymer, wherein the total amount of poly(ethylene)glycol in the nanoparticle is about 10 to about 30 weight percent poly(ethylene)glycol and about 0.2 to about 30 weight percent of Compound A.

20 Claims, 21 Drawing Sheets

POLYMERIC NANOPARTICLES AND METHODS OF MAKING AND USING SAME

CROSS-REFERENCE TO RELATED APPLICATIONS

This application is a U.S. National Phase application under 35 U.S.C. § 371 of PCT Application No. PCT/US2015/020086, filed Mar. 12, 2015, which published as WO 2015/142605 A1 on Sep. 24, 2015, and claims priority under 35 U.S.C. § 365(b) from U.S. provisional patent application No. 61/954,128, filed Mar. 17, 2014.

BACKGROUND OF THE INVENTION

Systems that deliver certain drugs to a patient (e.g., targeted to a particular tissue or cell type or targeted to a specific diseased tissue but not normal tissue) or that control release of drugs have long been recognized as beneficial.

For example, therapeutics that comprise an active drug and that are, e.g., targeted to a particular tissue or cell type or targeted to a specific diseased tissue but not to normal tissue, may reduce the amount of the drug in tissues of the body that are not targeted. This is particularly important when treating a condition such as cancer where it is desirable that a cytotoxic dose of the drug is delivered to cancer cells without killing the surrounding non-cancerous tissue. Effective drug targeting may reduce the undesirable and sometimes life threatening side effects common in anticancer therapy. In addition, such therapeutics may allow drugs to reach certain tissues they would otherwise be unable to reach.

Therapeutics that offer controlled release therapy also must be able to deliver an effective amount of drug, which is a known limitation in other nanoparticle delivery systems. For example, it can be a challenge to prepare nanoparticle systems that have an appropriate amount of drug associated with each nanoparticle, while keeping the size of the nanoparticles small enough to have advantageous delivery properties.

Accordingly, a need exists for nanoparticle therapeutics and methods of making such nanoparticles that are capable of delivering therapeutic levels of a therapeutic agent to potentially treat diseases such as cancer, while also reducing patient side effects.

SUMMARY OF THE INVENTION

Described herein are polymeric nanoparticles that comprise a small molecule compound that has potential of being a therapeutic agent, wherein said compound is 8-[4-(1-amino-cyclobutyl)phenyl]-9-phenyl-2H-[1,2,4]-triazolo-[3,4-f][1,6]-naphthyridin-3-one (hereinafter, "COMPOUND A" or "Comp. A"), or a pharmaceutically acceptable salt thereof. Further describes are methods of making and using such nanoparticles.

In one aspect, a nanoparticle is provided. The nanoparticle comprises about 50 to about 99.8 weight percent of a diblock poly(lactic) acid-poly(ethylene)glycol copolymer or a diblock poly(lactic acid-co-glycolic acid)-poly(ethylene) glycol copolymer, wherein the total amount of poly(ethylene)glycol in the nanoparticle is about 10 to about 30 weight percent poly(ethylene)glycol and about 0.2 to about 30 weight percent of a compound that is COMPOUND A represented by the formula:

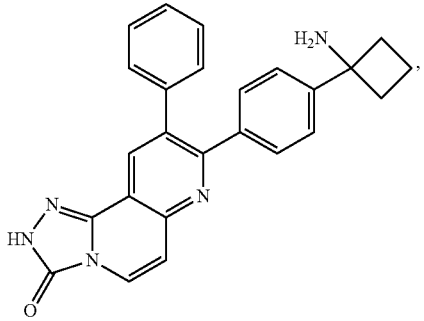 [SMILES: NC1(c2ccc(-c3nc4ccn5c(=O)[nH]nc5c4cc3-c3ccccc3)cc2)CCC1]

or a pharmaceutically acceptable salt thereof, wherein the nanoparticle releases about 0.01 to about 50% of the compound when placed in a phosphate buffer solution at room temperature for about 1 hour.

In another aspect, a nanoparticle is provided. The nanoparticle comprises about 50 to about 97.95 weight percent of a diblock poly(lactic) acid-poly(ethylene)glycol copolymer, wherein the total amount of poly(ethylene)glycol in the nanoparticle is about 10 to about 30 weight percent poly (ethylene)glycol, about 0.05 to about 35 weight percent of an organic acid selected from the group consisting of oleic acid and trifluoroacetic acid, and about 2 to about 30 weight percent of a compound that is COMPOUND A, or a pharmaceutically acceptable salt thereof.

In some embodiments, the poly(lactic) acid-poly(ethylene)glycol copolymer has a poly(lactic) acid number average molecular weight fraction of about 0.7 to about 0.9. In other embodiments, the poly(lactic) acid-poly(ethylene)glycol copolymer has a poly(lactic) acid number average molecular weight fraction of about 0.75 to about 0.85.

In certain embodiments, contemplated nanoparticles comprise about 10 to about 25 weight percent poly(ethylene) glycol. In other embodiments, contemplated nanoparticles comprise about 20 to about 30 weight percent poly(ethylene) glycol.

In some embodiments, the poly(lactic) acid-poly(ethylene)glycol copolymer has a number average molecular weight of about 15 kDa to about 20 kDa poly(lactic acid) and a number average molecular weight of about 4 kDa to about 6 kDa poly(ethylene)glycol. In other embodiments, the poly(lactic) acid-poly(ethylene)glycol copolymer has a number average molecular weight of about 16 kDa poly(lactic acid) and a number average molecular weight of about 5 kDa poly(ethylene)glycol.

In certain embodiments, contemplated nanoparticles comprise about 65 weight percent to about 85 weight percent of the copolymer.

In some embodiments, contemplated nanoparticles comprise a substantially hydrophobic acid. For example, contemplated nanoparticles may comprise about 0.05 to about 35 weight percent of a substantially hydrophobic acid, about 5 to about 15 weight percent of a substantially hydrophobic acid, or about 10 to about 20 weight percent of a substantially hydrophobic acid. In certain embodiments, the molar ratio of the substantially hydrophobic acid to the potential therapeutic agent is about 0.9:1 to about 1.1:1, wherein the acid is cholic acid. In other embodiments, the molar ratio of the substantially hydrophobic acid to the potential therapeutic agent is about 0.9:1 to about 1.1:1, wherein the acid is oleic acid.

In some embodiments, a $pK_a$ of the potential therapeutic agent is at least about 1.0 $pK_a$ unit greater than a $pK_a$ of the hydrophobic acid.

In certain embodiments, the substantially hydrophobic acid and the potential therapeutic agent form a hydrophobic ion pair in a contemplated nanoparticle for the potential use in therapy. In some embodiments, the hydrophobic acid is a bile acid. For example, in some embodiments, the bile acid is cholic acid. In other embodiments, the hydrophobic acid is oleic acid.

In some embodiments, contemplated nanoparticles comprise about 5 to about 20 weight percent of the therapeutic agent (e.g., about 6 to about 20 weight percent, about 7 to about 20 weight percent, about 8 to about 20 weight percent, and the like). In other embodiments, contemplated nanoparticles comprise about 10 to about 20 weight percent of the potential therapeutic agent.

In another aspect, a pharmaceutically acceptable composition is provided. The pharmaceutically acceptable composition comprises a plurality of contemplated nanoparticles and a pharmaceutically acceptable excipient.

In yet another aspect, a method of treating cancer (e.g., including, but not limited to, prostate cancer, breast cancer, and ovarian cancer) in a patient in need thereof is provided. The method comprises administering to the patient a therapeutically effective amount of a composition comprising nanoparticles contemplated herein.

DETAILED DESCRIPTION OF THE INVENTION

Figure 1:
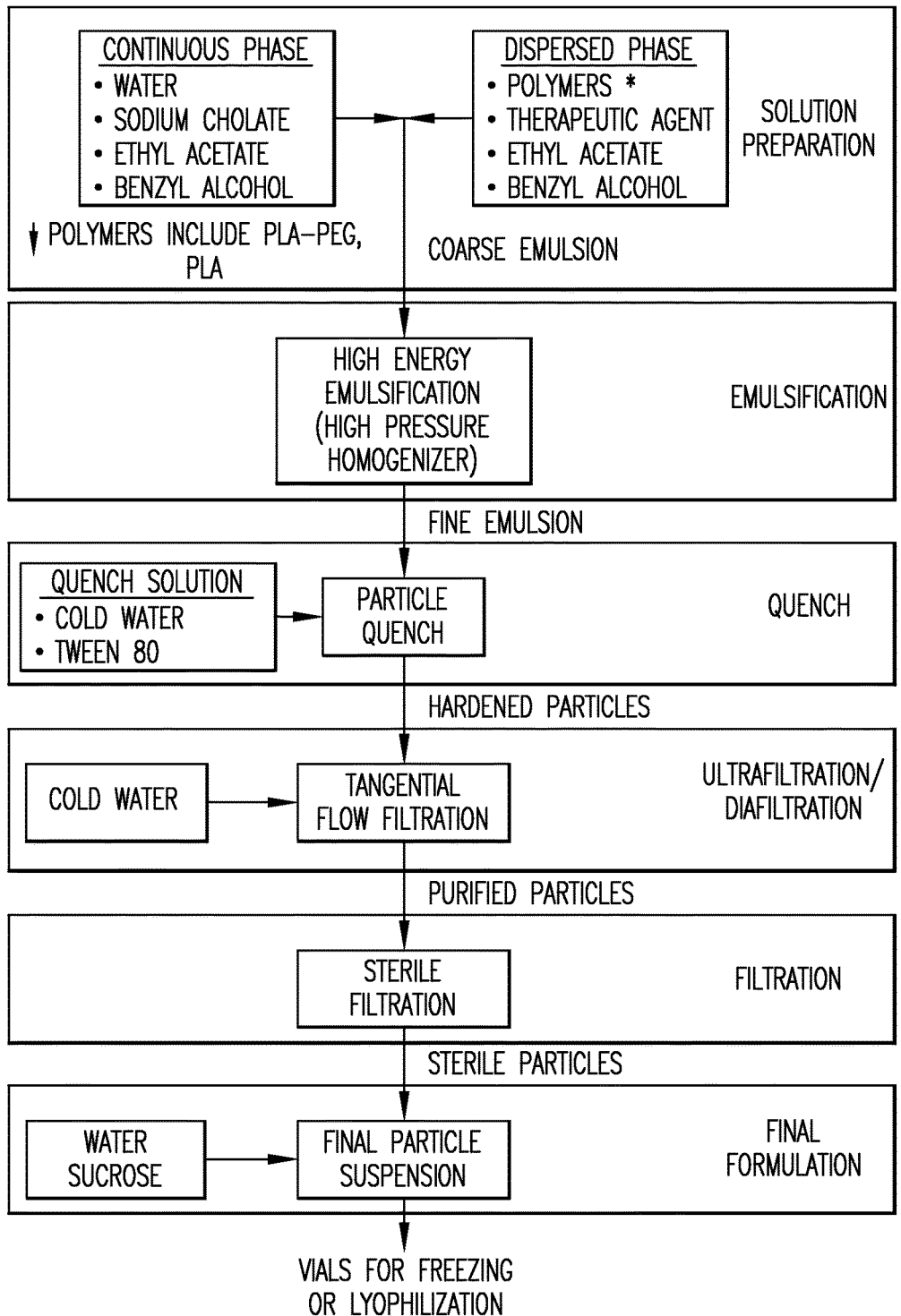
FIG. 1 is flow chart for an emulsion process for forming a disclosed nanoparticle.

Described herein are polymeric nanoparticles that comprise a potential therapeutic agent that is the small molecule compound 8-[4-(1-amino-cyclobutyl)phenyl]-9-phenyl-2H-[1,2,4]-triazolo-[3,4-f][1,6]-naphthyridin-3-one (i.e., COMPOUND A), or a pharmaceutically acceptable salt thereof, and methods of making and using such nanoparticles. In some embodiments, inclusion (i.e., doping) of a substantially hydrophobic acid (e.g., a bile acid) in a disclosed nanoparticle and/or included in a nanoparticle preparation process may result in nanoparticles that include improved drug loading. Furthermore, in certain embodiments, nanoparticles that include and/or are prepared in the presence of the hydrophobic acid may exhibit improved controlled release properties. For example, disclosed nanoparticles may more slowly release the potential therapeutic agent as compared to nanoparticles prepared in the absence of the hydrophobic acid.

Without wishing to be bound by any theory, nanoparticle formulations that include a hydrophobic acid (e.g., bile acid) may have significantly improved formulation properties (e.g., drug loading and/or release profile) through formation of a hydrophobic ion-pair (HIP), between the substantially hydrophobic acid and, e.g., the amine group of a potential therapeutic agent (e.g., a drug). As used herein, a HIP is a pair of oppositely charged ions held together by Coulombic attraction. Also without wishing to be bound by any theory, a HIP may be used to increase the hydrophobicity of a potential therapeutic agent. A potential therapeutic agent with increased hydrophobicity may be beneficial for nanoparticle formulations and result in HIP formation that may provide higher solubility of the potential therapeutic agent in organic solvents. HIP formation, as contemplated herein, can result in nanoparticles having for example, increased drug loading. Slower release of a potential therapeutic agent from the nanoparticles may also occur, for example in some embodiments, due to a decrease in the potential therapeutic agent's solubility in aqueous solution. Furthermore, complexing the potential therapeutic agent with large hydrophobic counter ions may slow diffusion of the potential therapeutic agent within the polymeric matrix. Advantageously, HIP formation occurs without the need for covalent conjugation of the hydrophobic group to the potential therapeutic agent.

Without wishing to be bound by any theory, it is believed that the strength of the HIP impacts the drug load and release rate of the contemplated nanoparticles. For example, the strength of the HIP may be increased by increasing the magnitude of the difference between the $pK_a$ of the therapeutic agent and the $pK_a$ of the hydrophobic acid, as discussed in more detail below. Also without wishing to be bound by any theory, it is believed that the conditions for ion pair formation impact the drug load and release rate of the contemplated nanoparticles.

Nanoparticles disclosed herein comprise one, two, three or more biocompatible and/or biodegradable polymers. For example, a contemplated nanoparticle may comprise about 35 to about 99.75 weight percent, in some embodiments about 50 to about 99.75 weight percent, in some embodiments about 50 to about 99.5 weight percent, in some embodiments about 50 to about 99 weight percent, in some embodiments about 50 to about 98 weight percent, in some embodiments about 50 to about 97 weight percent, in some embodiments about 50 to about 97.95 weight percent, in some embodiments about 50 to about 96 weight percent, in some embodiments about 50 to about 95 weight percent, in some embodiments about 50 to about 94 weight percent, in some embodiments about 50 to about 93 weight percent, in some embodiments about 50 to about 92 weight percent, in some embodiments about 50 to about 91 weight percent, in some embodiments about 50 to about 90 weight percent, in some embodiments about 50 to about 85 weight percent, in some embodiments about 50 to about 80 weight percent, and in some embodiments about 65 to about 85 weight percent of one or more block copolymers that include a biodegradable polymer and poly(ethylene glycol) (PEG), and about 0 to about 50 weight percent of a biodegradable homopolymer.

One embodiment relates to polymeric nanoparticles comprising a potential therapeutic agent, where the agent is an inhibitor of Akt, a serine/threonine protein kinase (i.e., protein kinase B). In some embodiments, the potential therapeutic agent is a compound that is 8-[4-(1-amino-cyclobutyl)phenyl]-9-phenyl-2H-[1,2,4]-triazolo-[3,4-f][1,6]-naphthyridin-3-one (i.e., COMPOUND A), represented by the formula:

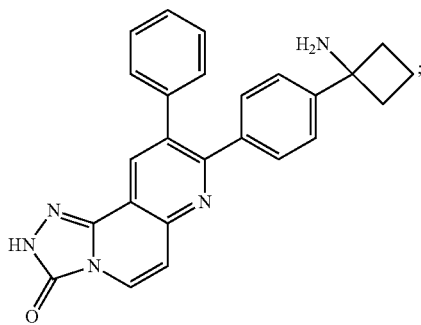 [SMILES: NC1(c2ccc(-c3nc4ccn5c(=O)[nH]nc5c4cc3-c3ccccc3)cc2)CCC1]

or a pharmaceutically acceptable salt thereof. In some embodiments, the potential therapeutic agent is a compound that is 8-[4-(1-amino-cyclobutyl)phenyl]-9-phenyl-2H-[1,2,4]-triazolo-[3,4-f][1,6]-naphthyridin-3-one dihydrochloride. Non-limiting examples of other Akt inhibitors include 4-(2-(4-amino-1,2,5-oxadiazol-3-yl)-1-ethyl-7-((S)-piperidin-3-ylmethoxy)-1H-imidazo[4,5-c]pyridin-4-yl)-2-methylbut-3-yn-2-ol (GSK690693), perifosine, (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one (GDC-0068), triciribine, triciribine phosphate, 4-amino-N-[(1S)-1-(4-chlorophenyl)-3-hydroxypropyl]-1-(7H-pyrrolo[2,3-d]pyrimidin-4-yl)-4-piperidinecarboxamide (AZD5363), 4-(4-chlorobenzyl)-1-(7H-pyrrolo[2,3-d]pyrimidin-4-yl)piperidin-4-amine (CCT128930), 4-dodecyl-N-(1,3,4-thiadiazol-2-yl)benzenesulfonamide (PHT-427), 4-(4-(1H-pyrazol-4-yl)phenyl)-4-(4-chlorophenyl)piperidine (AT7867), honokiol, (2S)-1-(5-(3-methyl-1H-indazol-5-yl)pyridin-3-yloxy)-3-phenylpropan-2-amine (A-674563), 2-amino-8-((1r,4r)-4-(2-hydroxyethoxy)cyclohexyl)-6-(6-methoxypyridin-3-yl)-4-methylpyrido[2,3-d]pyrimidin-7(8H)-one (PF-04691502), miltefosine, 7-benzyl-10-(2-methylbenzyl)-2,6,7,8,9,10-hexahydroimidazo[1,2-a]pyrido[4,3-d]pyrimidin-5(3H)-one (TIC10), and pharmaceutically acceptable salts thereof.

In some embodiments, disclosed nanoparticles may comprise about 0.2 to about 35 weight percent, about 0.2 to about 20 weight percent, about 0.2 to about 10 weight percent, about 0.2 to about 5 weight percent, about 0.5 to about 5 weight percent, about 0.75 to about 5 weight percent, about 1 to about 5 weight percent, about 2 to about 5 weight percent, about 3 to about 5 weight percent, about 1 to about 20 weight percent, about 2 to about 20 weight percent, about 5 to about 20 weight percent, about 1 to about 15 weight percent, about 2 to about 15 weight percent, about 3 to about 15 weight percent, about 4 to about 15 weight percent, about 5 to about 15 weight percent, about 1 to about 10 weight percent, about 2 to about 10 weight percent, about 3 to about 10 weight percent, about 4 to about 10 weight percent, about 5 to about 10 weight percent, about 10 to about 30 weight percent, or about 15 to about 25 weight percent of the potential therapeutic agent.

In certain embodiments, disclosed nanoparticles comprise a hydrophobic acid (e.g., a bile acid) and/or are prepared by a process that includes a hydrophobic acid. Such nanoparticles may have a higher drug loading than nanoparticles prepared by a process without a hydrophobic acid. For example, drug loading (e.g., by weight) of disclosed nanoparticles prepared by a process comprising the hydrophobic acid may be between about 2 times to about 10 times higher, or even more, than disclosed nanoparticles prepared by a process without the hydrophobic acid. In some embodiments, the drug loading (by weight) of disclosed nanoparticles prepared by a first process comprising the hydrophobic acid may be at least about 2 times higher, at least about 3 times higher, at least about 4 times higher, at least about 5 times higher, or at least about 10 times higher than disclosed nanoparticles prepared by a second process, where the second process is identical to the first process except that the second process does not include the hydrophobic acid.

Any suitable hydrophobic acid is contemplated. In some embodiments, the hydrophobic acid may be a carboxylic acid (e.g., a monocarboxylic acid, dicarboxylic acid, tricarboxylic acid, or the like), a sulfinic acid, a sulfenic acid, or a sulfonic acid. In some cases, a contemplated hydrophobic acid may include a mixture of two or more acids. In some cases, a salt of a hydrophobic acid may be used in a formulation.

For example, a disclosed carboxylic acid may be an aliphatic carboxylic acid (e.g., a carboxylic acid having a cyclic or acyclic, branched or unbranched, hydrocarbon chain). Disclosed carboxylic acids may, in some embodiments, be substituted with one or more functional groups including, but not limited to, halogen (i.e., F, Cl, Br, and I), sulfonyl, nitro, and oxo. In certain embodiments, a disclosed carboxylic acid may be unsubstituted.

Exemplary carboxylic acids may include a substituted or unsubstituted fatty acid (e.g., $C_6$-$C_{50}$ fatty acid). In some instances, the fatty acid may be a $C_{10}$-$C_{20}$ fatty acid. In other instances, the fatty acid may be a $C_{15}$-$C_{20}$ fatty acid. The fatty acid may, in some cases, be saturated. In other embodiments, the fatty acid may be unsaturated. For instance, the fatty acid may be a monounsaturated fatty acid or a polyunsaturated fatty acid. In some embodiments, a double bond of an unsaturated fatty acid group can be in the cis conformation. In some embodiments, a double bond of an unsaturated fatty acid can be in the trans conformation. Unsaturated fatty acids include, but are not limited to, omega-3, omega-6, and omega-9 fatty acids.

Non-limiting examples of saturated fatty acids include caproic acid, enanthic acid, caprylic acid, pelargonic acid, capric acid, undecanoic acid, lauric acid, tridecanoic acid, myristic acid, pentadecanoic acid, palmitic acid, margaric acid, stearic acid, nonadecanoic acid, arachidic acid, heneicosanoic acid, behenic acid, tricosanoic acid, lignoceric acid, pentacosanoic acid, cerotic acid, heptacosanoic acid, montanic acid, nonacosanoic acid, melissic acid, henatriacontanoic acid, lacceroic acid, psyllic acid, geddic acid, ceroplastic acid, hexatriacontanoic acid, and combinations thereof.

Non-limiting examples of unsaturated fatty acids include hexadecatrienoic acid, alpha-linolenic acid, stearidonic acid, eicosatrienoic acid, eicosatetraenoic acid, eicosapentaenoic acid, heneicosapentaenoic acid, docosapentaenoic acid, docosahexaenoic acid, tetracosapentaenoic acid, tetracosahexaenoic acid, linoleic acid, gamma-linolenic acid, eicosadienoic acid, dihomo-gamma-linolenic acid, arachidonic acid, docosadienoic acid, adrenic acid, docosapentaenoic acid, tetracosatetraenoic acid, tetracosapentaenoic acid, oleic acid ($pK_a$=~4-5; log P=6.78), eicosenoic acid, mead acid, erucic acid, nervonic acid, rumenic acid, α-calendic acid, β-calendic acid, jacaric acid, α-eleostearic acid, β-eleostearic acid, catalpic acid, punicic acid, rumelenic acid, α-parinaric acid, β-parinaric acid, bosseopentaenoic acid, pinolenic acid, podocarpic acid, palmitoleic acid, vaccenic acid, gadoleic acid, erucic acid, and combinations thereof.

Other non-limiting examples of hydrophobic acids include aromatic acids, such as 1-hydroxy-2-naphthoic acid (i.e., xinafoic acid) ($pK_a$, =~2-3; log P=2.97), naphthalene-1,5-disulfonic acid ($pK_a$, =~2; log P=1.3), naphthalene-2-sulfonic acid ($pK_a$=~1.8; log P=2.1), pamoic acid ($pK_a$, = 2.4), cinnamic acid, phenylacetic acid, (±)-camphor-10-sulfonic acid, dodecylbenzenesulfonic acid ($pK_a$, =~1.8; log P=6.6), and combinations thereof. Other non-limiting examples of hydrophobic acids include dodecylsulfuric acid ($pK_a$=~0.09; log P=4.5), dioctyl sulfosuccinic acid ($pK_a$, = ~0.8; log P=5.2), dioleoyl phosphatidic acid ($pK_a$=~2), and Vitamin $D_3$-sulfate ($pK_a$, =~1.5).

In some embodiments, the hydrophobic acid may be a bile acid. Non-limiting examples of bile acids include chenodeoxycholic acid, ursodeoxycholic acid, deoxycholic acid ($pK_a$, =4.65; log P=3.79), hycholic acid, beta-muricholic acid, cholic acid ($pK_a$=~4.5; log P=2.48), taurocholic acid, cholesteryl sulfate ($pK_a$=~1.4), lithocholic acid, an amino acid-conjugated bile acid, and combinations thereof. An amino-acid conjugated bile acid may be conjugated to any suitable amino acid. In some embodiments, the amino acid-conjugated bile acid is a glycine-conjugated bile acid or a taurine-conjugated bile acid.

In certain instances, the hydrophobic acid may be a polyelectrolyte. For example, the polyelectrolyte may be a polysulfonic acid (e.g., poly(styrene sulfonic acid) or dextran sulfate) or a polycarboxylic acid (e.g., polypolyacrylic acid or polymethacrylic acid).

In some instances, a contemplated acid may have a molecular weight of less than about 1000 Da, in some embodiments less than about 500 Da, in some embodiments less than about 400 Da, in some embodiments less than about 300 Da, in some embodiments less than about 250 Da, in some embodiments less than about 200 Da, and in some embodiments less than about 150 Da. In some cases, the acid may have a molecular weight of between about 100 Da and about 1000 Da, in some embodiments between about 200 Da and about 800 Da, in some embodiments between about 200 Da and about 600 Da, in some embodiments between about 100 Da and about 300 Da, in some embodiments between about 200 Da and about 400 Da, in some embodiments between about 300 Da and about 500 Da, and in some embodiments between about 300 Da and about 1000 Da. In certain embodiments, a contemplated acid may have a molecular weight of greater than about 300 Da, in some embodiments greater than 400 Da, and in some embodiments greater than 500 Da. In certain embodiments, the release rate of a therapeutic agent from a nanoparticle can be slowed by increasing the molecular weight of the hydrophobic acid used in the nanoparticle formulation.

In some embodiments, a hydrophobic acid may be chosen, at least in part, on the basis of the strength of the acid. For example, the hydrophobic acid may have an acid dissociation constant in water ($pK_a$) of about −5 to about 7, in some embodiments about −3 to about 5, in some embodiments about −3 to about 4, in some embodiments about −3 to about 3.5, in some embodiments about −3 to about 3, in some embodiments about −3 to about 2, in some embodiments about −3 to about 1, in some embodiments about −3 to about 0.5, in some embodiments about −0.5 to about 0.5, in some embodiments about 1 to about 7, in some embodiments about 2 to about 7, in some embodiments about 3 to about 7, in some embodiments about 4 to about 6, in some embodiments about 4 to about 5.5, in some embodiments about 4 to about 5, and in some embodiments about 4.5 to about 5, determined at 25° C. In some embodiments, the acid may have a $pK_a$ of less than about 7, less than about 5, less than about 3.5, less than about 3, less than about 2, less than about 1, or less than about 0, determined at 25° C.

In certain embodiments, the hydrophobic acid may be chosen, at least in part, on the basis of the difference between the $pK_a$ of the hydrophobic acid and the $pK_a$ of a protonated nitrogen-containing therapeutic agent. For example, in some instances, the difference between the $pK_a$ of the hydrophobic acid and the $pK_a$ of a protonated nitrogen-containing therapeutic agent may be between about 1 $pK_a$ unit and about 15 $pK_a$ units, in some embodiments between about 1 $pK_a$ unit and about 10 $pK_a$ units, in some embodiments between about 1 $pK_a$ unit and about 5 $pK_a$ units, in some embodiments between about 1 $pK_a$ unit and about 3 $pK_a$ units, in some embodiments between about 1 $pK_a$ unit and about 2 $pK_a$ units, in some embodiments between about 2

$pK_a$, units and about 15 $pK_a$ units, in some embodiments between about 2 $pK_a$ units and about 10 $pK_a$ units, in some embodiments between about 2 $pK_a$, units and about 5 $pK_a$ $pK_a$, units, in some embodiments between about 2 $pK_a$, units and about 3 $pK_a$, units, in some embodiments between about 3 $pK_a$, units and about 15 $pK_a$, units, in some embodiments between about 3 $pK_a$ units and about 10 $pK_a$ units, in some embodiments between about 3 $pK_a$ units and about 5 $pK_a$, units, in some embodiments between about 4 $pK_a$ units and about 15 $pK_a$ units, in some embodiments between about 4 $pK_a$, units and about 10 $pK_a$, units, in some embodiments between about 4 $pK_a$, units and about 6 $pK_a$, units, in some embodiments between about 5 $pK_a$ units and about 15 $pK_a$ units, in some embodiments between about 5 $pK_a$, units and about 10 $pK_a$ units, in some embodiments between about 5 $pK_a$ units and about 7 $pK_a$, units, in some embodiments between about 7 $pK_a$ units and about 15 $pK_a$ units, in some embodiments between about 7 $pK_a$, units and about 9 $pK_a$, units, in some embodiments between about 9 $pK_a$ units and about 15 $pK_a$ units, in some embodiments between about 9 $pK_a$, units and about 11 $pK_a$, units, in some embodiments between about 11 $pK_a$, units and about 13 $pK_a$ units, and in some embodiments between about 13 $pK_a$, units and about 15 $pK_a$, units, determined at 25° C.

In some instances, the difference between the $pK_a$ of the hydrophobic acid and the $pK_a$, of a protonated nitrogen-containing therapeutic agent may be at least about 1 $pK_a$, unit, in some embodiments at least about 2 $pK_a$, units, in some embodiments at least about 3 $pK_a$, units, in some embodiments at least about 4 $pK_a$, units, in some embodiments at least about 5 $pK_a$, units, in some embodiments at least about 6 $pK_a$, units, in some embodiments at least about 7 $pK_a$ units, in some embodiments at least about 8 $pK_a$ units, in some embodiments at least about 9 $pK_a$, units, in some embodiments at least about 10 $pK_a$, units, and in some embodiments at least about 15 $pK_a$, units, determined at 25° C.

In some embodiments, the hydrophobic acid may have a log P of between about 2 and about 15, in some embodiments between about 5 and about 15, in some embodiments between about 5 and about 10, in some embodiments between about 2 and about 8, in some embodiments between about 4 and about 8, in some embodiments between about 2 and about 7, or in some embodiments between about 4 and about 7. In some instances, the hydrophobic acid may have a log P greater than about 2, greater than about 4, greater than about 5, or greater than 6.

In some embodiments, a contemplated hydrophobic acid may have a phase transition temperature that is advantageous, for example, for improving the properties of the therapeutic nanoparticles. For instance, the acid may have a melting point of less than about 300° C., in some cases less than about 100° C., and in some cases less than about 50° C. In certain embodiments, the acid may have a melting point of between about 5° C. and about 25° C., in some cases between about 15° C. and about 50° C., in some cases between about 30° C. and about 100° C., in some cases between about 75° C. and about 150° C., in some cases between about 125° C. and about 200° C., in some cases between about 150° C. and about 250° C., and in some cases between about 200° C. and about 300° C. In some cases, the acid may have a melting point of less than about 15° C., in some cases less than about 10° C., or in some cases less than about 0° C. In certain embodiments, the acid may have a melting point of between about −30° C. and about 0° C. or in some cases between about −20° C. and about −10° C.

For example, an acid for use in methods and nanoparticles disclosed herein may be chosen, at least in part, on the basis of the solubility of the therapeutic agent in a solvent comprising the acid. For example, in some embodiments, the therapeutic agent dissolved in a solvent comprising the acid may have a solubility of between about 15 mg/mL to about 200 mg/mL, between about 20 mg/mL to about 200 mg/mL, between about 25 mg/mL to about 200 mg/mL, between about 50 mg/mL to about 200 mg/mL, between about 75 mg/mL to about 200 mg/mL, between about 100 mg/mL to about 200 mg/mL, between about 125 mg/mL to about 175 mg/mL, between about 15 mg/mL to about 50 mg/mL, between about 25 mg/mL to about 75 mg/mL. In some embodiments, the potential therapeutic agent dissolved in a solvent comprising the acid may have a solubility greater than about 10 mg/mL, greater than about 50 mg/mL, or greater than about 100 mg/mL. In some embodiments, the potential therapeutic agent dissolved in a solvent comprising the hydrophobic acid (e.g., a first solution consisting of the therapeutic agent, solvent, and hydrophobic acid) may have a solubility of at least about 2 times greater, in some embodiments at least about 5 times greater, in some embodiments at least about 10 times greater, in some embodiments at least about 20 times greater, in some embodiments about 2 times to about 20 times greater or in some embodiments about 10 times to about 20 times greater than when the potential therapeutic agent is dissolved in a solvent that does not contain the hydrophobic acid (e.g., a second solution consisting of the potential therapeutic agent and the solvent).

In some instances, the concentration of acid in a drug solution (i.e., solution of potential therapeutic agent) may be between about 1 weight percent and about 30 weight percent, in some embodiments between about 2 weight percent and about 30 weight percent, in some embodiments between about 3 weight percent and about 30 weight percent, in some embodiments between about 4 weight percent and about 30 weight percent, in some embodiments between about 5 weight percent and about 30 weight percent, in some embodiments between about 6 weight percent and about 30 weight percent, in some embodiments between about 8 weight percent and about 30 weight percent, in some embodiments between about 10 weight percent and about 30 weight percent, in some embodiments between about 12 weight percent and about 30 weight percent, in some embodiments between about 14 weight percent and about 30 weight percent, in some embodiments between about 16 weight percent and about 30 weight percent, in some embodiments between about 1 weight percent and about 5 weight percent, in some embodiments between about 3 weight percent and about 9 weight percent, in some embodiments between about 6 weight percent and about 12 weight percent, in some embodiments between about 9 weight percent and about 15 weight percent, in some embodiments between about 12 weight percent and about 18 weight percent, and in some embodiments between about 15 weight percent and about 21 weight percent. In certain embodiments, the concentration of hydrophobic acid in a drug solution may be at least about 1 weight percent, in some embodiments at least about 2 weight percent, in some embodiments at least about 3 weight percent, in some embodiments at least about 5 weight percent, in some embodiments at least about 10 weight percent, in some embodiments at least about 15 weight percent, and in some embodiments at least about 20 weight percent.

In certain embodiments, the molar ratio of hydrophobic acid to potential therapeutic agent (e.g., initially during formulation of the nanoparticles and/or in the nanoparticles)

may be between about 0.25:1 to about 6:1, in some embodiments between about 0.25:1 to about 5:1, in some embodiments between about 0.25:1 to about 4:1, in some embodiments between about 0.25:1 to about 3:1, in some embodiments between about 0.25:1 to about 2:1, in some embodiments between about 0.25:1 to about 1.5:1, in some embodiments between about 0.25:1 to about 1:1, in some embodiments between about 0.25:1 to about 0.5:1, in some embodiments between about 0.5:1 to about 6:1, in some embodiments between about 0.5:1 to about 5:1, in some embodiments between about 0.5:1 to about 4:1, in some embodiments between about 0.5:1 to about 3:1, in some embodiments between about 0.5:1 to about 2:1, in some embodiments between about 0.5:1 to about 1.5:1, in some embodiments between about 0.5:1 to about 1:1, in some embodiments between about 0.5:1 to about 0.75:1, in some embodiments between about 0.75:1 to about 2:1, in some embodiments between about 0.75:1 to about 1.5:1, in some embodiments between about 0.75:1 to about 1.25:1, in some embodiments between about 0.75:1 to about 1:1, in some embodiments between about 1:1 to about 6:1, in some embodiments between about 1:1 to about 5:1, in some embodiments between about 1:1 to about 4:1, in some embodiments between about 1:1 to about 3:1, in some embodiments between about 1:1 to about 2:1, in some embodiments between about 1:1 to about 1.5:1, in some embodiments between about 1.5:1 to about 6:1, in some embodiments between about 1.5:1 to about 5:1, in some embodiments between about 1.5:1 to about 4:1, in some embodiments between about 1.5:1 to about 3:1, in some embodiments between about 2:1 to about 6:1, in some embodiments between about 2:1 to about 4:1, in some embodiments between about 3:1 to about 6:1, in some embodiments between about 3:1 to about 5:1, and in some embodiments between about 4:1 to about 6:1.

In some instances, the initial molar ratio of hydrophobic acid to potential therapeutic agent (i.e., during formulation of the nanoparticles) may be different from the molar ratio of hydrophobic acid to potential therapeutic agent in the nanoparticles (i.e., after removal of unencapsulated hydrophobic acid and therapeutic agent). In other instances, the initial molar ratio of hydrophobic acid to potential therapeutic agent (i.e., during formulation of the nanoparticles) may be essentially the same as the molar ratio of hydrophobic acid to potential therapeutic agent in the nanoparticles (i.e., after removal of unencapsulated hydrophobic acid and potential therapeutic agent).

In some cases, a solution containing the potential therapeutic agent may be prepared separately from a solution containing the polymer, and the two solutions may then be combined prior to nanoparticle formulation. For instance, in one embodiment, a first solution contains the potential therapeutic agent and the hydrophobic acid, and a second solution contains the polymer and optionally the hydrophobic acid. Formulations where the second solution does not contain the hydrophobic acid may be advantageous, for example, for minimizing the amount of hydrophobic acid used in a process or, in some cases, for minimizing contact time between the hydrophobic acid and, e.g., a polymer that can degrade in the presence of the hydrophobic acid. In other cases, a single solution may be prepared containing the potential therapeutic agent, polymer, and hydrophobic acid.

In some embodiments, the hydrophobic ion pair may be formed prior to formulation of the nanoparticles. For example, a solution containing the hydrophobic ion pair may be prepared prior to formulating the contemplated nanoparticles (e.g., by preparing a solution containing suitable amounts of the potential therapeutic agent and the hydrophobic acid). In other embodiments, the hydrophobic ion pair may be formed during formulation of the nanoparticles. For example, a first solution containing the potential therapeutic agent and a second solution containing the hydrophobic acid may be combined during a process step for preparing the nanoparticles (e.g., prior to emulsion formation and/or during emulation formation). In certain embodiments, the hydrophobic ion pair may form prior to encapsulation of the potential therapeutic agent and hydrophobic acid in a contemplated nanoparticle. In other embodiments, the hydrophobic ion pair may form in the nanoparticle, e.g., after encapsulation of the potential therapeutic agent and hydrophobic acid.

In certain embodiments, the hydrophobic acid may have a solubility of less than about 2 g per 100 mL of water, in some embodiments less than about 1 g per 100 mL of water, in some embodiments less than about 100 mg per 100 mL of water, in some embodiments less than about 10 mg per 100 mL of water, and in some embodiments less than about 1 mg per 100 mL of water, determined at 25° C. In other embodiments, the acid may have a solubility of between about 1 mg per 100 mL of water to about 2 g per 100 mL of water, in some embodiments between about 1 mg per 100 mL of water to about 1 g per 100 mL of water, in some embodiments between about 1 mg per 100 mL of water to about 500 mg per 100 mL of water, and in some embodiments between about 1 mg per 100 mL of water to about 100 mg per 100 mL of water, determined at 25° C. In some embodiments, the hydrophobic acid may be essentially insoluble in water at 25° C.

In some embodiments, disclosed nanoparticles may be essentially free of the hydrophobic acid used during the preparation of the nanoparticles. In other embodiments, disclosed nanoparticles may comprise the hydrophobic acid. For instance, in some embodiments, the acid content in disclosed nanoparticles may be between about 0.05 weight percent to about 30 weight percent, in some embodiments between about 0.5 weight percent to about 30 weight percent, in some embodiments between about 1 weight percent to about 30 weight percent, in some embodiments between about 2 weight percent to about 30 weight percent, in some embodiments between about 3 weight percent to about 30 weight percent, in some embodiments between about 5 weight percent to about 30 weight percent, in some embodiments between about 7 weight percent to about 30 weight percent, in some embodiments between about 10 weight percent to about 30 weight percent, in some embodiments between about 15 weight percent to about 30 weight percent, in some embodiments between about 20 weight percent to about 30 weight percent, in some embodiments between about 0.05 weight percent to about 0.5 weight percent, in some embodiments between about 0.05 weight percent to about 5 weight percent, in some embodiments between about 1 weight percent to about 5 weight percent, in some embodiments between about 3 weight percent to about 10 weight percent, in some embodiments between about 5 weight percent to about 15 weight percent, and in some embodiments between about 10 weight percent to about 20 weight percent.

In some embodiments, disclosed nanoparticles substantially immediately release (e.g., over about 1 minute to about 30 minutes, about 1 minute to about 25 minutes, about 5 minutes to about 30 minutes, about 5 minutes to about 1 hour, about 1 hour, or about 24 hours) less than about 2%, less than about 5%, less than about 10%, less than about 15%, less than about 20%, less than about 25%, less than about 30%, or less than 40% of the potential therapeutic agent, for example when placed in a phosphate buffer solution at room temperature (e.g., 25° C.) and/or at 37° C. In certain embodiments, nanoparticles comprising the therapeutic agent may release the potential therapeutic agent when placed in an aqueous solution (e.g., a phosphate buffer solution), e.g., at 25° C. and/or at 37° C., at a rate substantially corresponding to about 0.01 to about 50%, in some embodiments about 0.01 to about 25%, in some embodiments about 0.01 to about 15%, in some embodiments about 0.01 to about 10%, in some embodiments about 1 to about 40%, in some embodiments about 5 to about 40%, and in some embodiments about 10 to about 40% of the potential therapeutic agent released over about 1 hour. In some embodiments, nanoparticles comprising the therapeutic agent may release the potential therapeutic agent when placed in an aqueous solution (e.g., a phosphate buffer solution), e.g., at 25° C. and/or at 37° C., at a rate substantially corresponding to about 10 to about 70%, in some embodiments about 10 to about 45%, in some embodiments about 10 to about 35%, or in some embodiments about 10 to about 25%, of the therapeutic agent released over about 4 hours.

In some embodiments, disclosed nanoparticles may substantially retain the potential therapeutic agent, e.g., for at least about 1 minute, at least about 1 hour, or more, when placed in a phosphate buffer solution at 37° C.

In general, a "nanoparticle" refers to any particle having a diameter of less than 1000 nm, e.g., about 10 nm to about 200 nm. Disclosed therapeutic nanoparticles may include nanoparticles having a diameter of about 60 to about 120 nm, or about 70 to about 120 nm, or about 80 to about 120 nm, or about 90 to about 120 nm, or about 100 to about 120 nm, or about 60 to about 130 nm, or about 70 to about 130 nm, or about 80 to about 130 nm, or about 90 to about 130 nm, or about 100 to about 130 nm, or about 110 to about 130 nm, or about 60 to about 140 nm, or about 70 to about 140 nm, or about 80 to about 140 nm, or about 90 to about 140 nm, or about 100 to about 140 nm, or about 110 to about 140 nm, or about 60 to about 150 nm, or about 70 to about 150 nm, or about 80 to about 150 nm, or about 90 to about 150 nm, or about 100 to about 150 nm, or about 110 to about 150 nm, or about 120 to about 150 nm.

Polymers

In some embodiments, the nanoparticles may comprise a matrix of polymers and a potential therapeutic agent. In some embodiments, a potential therapeutic agent can be associated with at least part of the polymeric matrix. The potential therapeutic agent can be associated with the surface of, encapsulated within, surrounded by, and/or dispersed throughout the polymeric matrix.

Any suitable polymer can be used in the disclosed nanoparticles. Polymers can be natural or unnatural (synthetic) polymers. Polymers can be homopolymers or copolymers comprising two or more monomers. In terms of sequence, copolymers can be random, block, or comprise a combination of random and block sequences. Typically, polymers are organic polymers.

The term "polymer," as used herein, is given its ordinary meaning as used in the art, i.e., a molecular structure comprising one or more repeat units (monomers), connected by covalent bonds. The repeat units may all be identical, or in some cases, there may be more than one type of repeat unit present within the polymer. In some cases, the polymer can be biologically derived, i.e., a biopolymer. Non-limiting examples include peptides or proteins. In some cases, additional moieties may also be present in the polymer, for example biological moieties such as those described below. If more than one type of repeat unit is present within the polymer, then the polymer is said to be a "copolymer." It is to be understood that in any embodiment employing a polymer, the polymer being employed may be a copolymer in some cases. The repeat units forming the copolymer may be arranged in any fashion. For example, the repeat units may be arranged in a random order, in an alternating order, or as a block copolymer, i.e., comprising one or more regions each comprising a first repeat unit (e.g., a first block), and one or more regions each comprising a second repeat unit (e.g., a second block), etc. Block copolymers may have two (a diblock copolymer), three (a triblock copolymer), or more numbers of distinct blocks.

Disclosed particles can include copolymers, which, in some embodiments, describes two or more polymers (such as those described herein) that have been associated with each other, usually by covalent bonding of the two or more polymers together. Thus, a copolymer may comprise a first polymer and a second polymer, which have been conjugated together to form a block copolymer where the first polymer can be a first block of the block copolymer and the second polymer can be a second block of the block copolymer. Of course, those of ordinary skill in the art will understand that a block copolymer may, in some cases, contain multiple blocks of polymer, and that a "block copolymer," as used herein, is not limited to only block copolymers having only a single first block and a single second block. For instance, a block copolymer may comprise a first block comprising a first polymer, a second block comprising a second polymer, and a third block comprising a third polymer or the first polymer, etc. In some cases, block copolymers can contain any number of first blocks of a first polymer and second blocks of a second polymer (and in certain cases, third blocks, fourth blocks, etc.). In addition, it should be noted that block copolymers can also be formed, in some instances, from other block copolymers. For example, a first block copolymer may be conjugated to another polymer (which may be a homopolymer, a biopolymer, another block copolymer, etc.), to form a new block copolymer containing multiple types of blocks, and/or to other moieties (e.g., to non-polymeric moieties).

In some embodiments, the polymer (e.g., copolymer, e.g., block copolymer) can be amphiphilic, i.e., having a hydrophilic portion and a hydrophobic portion, or a relatively hydrophilic portion and a relatively hydrophobic portion. A hydrophilic polymer can be one generally that attracts water and a hydrophobic polymer can be one that generally repels water. A hydrophilic or a hydrophobic polymer can be identified, for example, by preparing a sample of the polymer and measuring its contact angle with water (typically, the polymer will have a contact angle of less than 60°, while a hydrophobic polymer will have a contact angle of greater than about 60°). In some cases, the hydrophilicity of two or more polymers may be measured relative to each other, i.e., a first polymer may be more hydrophilic than a second polymer. For instance, the first polymer may have a smaller contact angle than the second polymer.

In one set of embodiments, a polymer (e.g., copolymer, e.g., block copolymer) contemplated herein includes a biocompatible polymer, i.e., the polymer that does not typically induce an adverse response when inserted or injected into a living subject, for example, without significant inflammation and/or acute rejection of the polymer by the immune system, for instance, via a T-cell response. Accordingly, the nanoparticles contemplated herein can be non-immunogenic. The term non-immunogenic as used herein refers to endogenous growth factor in its native state which normally elicits no, or only minimal levels of, circulating antibodies, T-cells, or reactive immune cells, and which normally does not elicit in the individual an immune response against itself.

Biocompatibility typically refers to the acute rejection of material by at least a portion of the immune system, i.e., a nonbiocompatible material implanted into a subject provokes an immune response in the subject that can be severe enough such that the rejection of the material by the immune system cannot be adequately controlled, and often is of a degree such that the material must be removed from the subject. One simple test to determine biocompatibility can be to expose a polymer to cells in vitro; biocompatible polymers are polymers that typically will not result in significant cell death at moderate concentrations, e.g., at concentrations of 50 micrograms/$10^6$ cells. For instance, a biocompatible polymer may cause less than about 20% cell death when exposed to cells such as fibroblasts or epithelial cells, even if phagocytosed or otherwise uptaken by such cells. Non-limiting examples of biocompatible polymers that may be useful in various embodiments include polydioxanone (PDO), polyhydroxyalkanoate, polyhydroxybutyrate, poly(glycerol sebacate), polyglycolide (i.e., poly(glycolic) acid) (PGA), polylactide (i.e., poly(lactic) acid) (PLA), poly(lactic) acid-co-poly(glycolic) acid (PLGA), polycaprolactone, or copolymers or derivatives including these and/or other polymers.

In certain embodiments, contemplated biocompatible polymers may be biodegradable, i.e., the polymer is able to degrade, chemically and/or biologically, within a physiological environment, such as within the body. As used herein, "biodegradable" polymers are those that, when introduced into cells, are broken down by the cellular machinery (biologically degradable) and/or by a chemical process, such as hydrolysis, (chemically degradable) into components that the cells can either reuse or dispose of without significant toxic effect on the cells. In one embodiment, the biodegradable polymer and their degradation byproducts can be biocompatible.

Particles disclosed herein may or may not contain PEG. In addition, certain embodiments can be directed towards copolymers containing poly(ester-ether)s, e.g., polymers having repeat units joined by ester bonds (e.g., R—C(O)—O—R' bonds) and ether bonds (e.g., R—O—R' bonds). In some embodiments, a biodegradable polymer, such as a hydrolyzable polymer, containing carboxylic acid groups, may be conjugated with poly(ethylene glycol) repeat units to form a poly(ester-ether). A polymer (e.g., copolymer, e.g., block copolymer) containing poly(ethylene glycol) repeat units can also be referred to as a "PEGylated" polymer.

For instance, a contemplated polymer may be one that hydrolyzes spontaneously upon exposure to water (e.g., within a subject), or the polymer may degrade upon exposure to heat (e.g., at temperatures of about 37° C.). Degradation of a polymer may occur at varying rates, depending on the polymer or copolymer used. For example, the half-life of the polymer (the time at which 50% of the polymer can be degraded into monomers and/or other nonpolymeric moieties) may be on the order of days, weeks, months, or years, depending on the polymer. The polymers may be biologically degraded, e.g., by enzymatic activity or cellular machinery, in some cases, for example, through exposure to a lysozyme (e.g., having relatively low pH). In some cases, the polymers may be broken down into monomers and/or other nonpolymeric moieties that cells can either reuse or dispose of without significant toxic effect on the cells (for example, polylactide may be hydrolyzed to form lactic acid, polyglycolide may be hydrolyzed to form glycolic acid, etc.).

In some embodiments, polymers may be polyesters, including copolymers comprising lactic acid and glycolic acid units, such as poly(lactic acid-co-glycolic acid) and poly(lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids; PEGylated polymers and copolymers of lactide and glycolide (e.g., PEGylated PLA, PEGylated PGA, PEGylated PLGA, and derivatives thereof). In some embodiments, polyesters include, for example, polyanhydrides, poly(ortho ester) PEGylated poly(ortho ester), poly(caprolactone), PEGylated poly(caprolactone), polylysine, PEGylated polylysine, poly(ethylene imine), PEGylated poly(ethylene imine), poly(L-lactide-co-L-lysine), poly(serine ester), poly(4-hydroxy-L-proline ester), poly[α-(4-aminobutyl)-L-glycolic acid], and derivatives thereof.

In some embodiments, a polymer may be PLGA. PLGA is a biocompatible and biodegradable co-polymer of lactic acid and glycolic acid, and various forms of PLGA can be characterized by the ratio of lactic acid:glycolic acid. Lactic acid can be L-lactic acid, D-lactic acid, or D,L-lactic acid. The degradation rate of PLGA can be adjusted by altering the lactic acid-glycolic acid ratio. In some embodiments, PLGA can be characterized by a lactic acid:glycolic acid ratio of approximately 85:15, approximately 75:25, approximately 60:40, approximately 50:50, approximately 40:60, approximately 25:75, or approximately 15:85. In some embodiments, the ratio of lactic acid to glycolic acid monomers in the polymer of the particle (e.g., the PLGA block copolymer or PLGA-PEG block copolymer), may be selected to optimize for various parameters such as water uptake, agent release and/or polymer degradation kinetics can be optimized.

In some embodiments, polymers may be one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, amino alkyl methacrylate copolymer, poly(acrylic acid), poly(methacrylic acid), methacrylic acid alkylamide copolymer, poly(methyl methacrylate), poly(methacrylic acid polyacrylamide, amino alkyl methacrylate copolymer, glycidyl methacrylate copolymers, polycyanoacrylates, and combinations comprising one or more of the foregoing polymers. The acrylic polymer may comprise fully-polymerized copolymers of acrylic and methacrylic acid esters with a low content of quaternary ammonium groups.

In some embodiments, polymers can be cationic polymers. In general, cationic polymers are able to condense and/or protect negatively charged strands of nucleic acids (e.g., DNA, RNA, or derivatives thereof). Amine-containing polymers such as poly(lysine), polyethylene imine (PEI), and poly(amidoamine) dendrimers are contemplated for use, in some embodiments, in a disclosed particle.

In some embodiments, polymers can be degradable polyesters bearing cationic side chains. Examples of these polyesters include poly(L-lactide-co-L-lysine), poly(serine ester), poly(4-hydroxy-L-proline ester).

It is contemplated that PEG may be terminated and include an end group. For example, PEG may terminate in a hydroxyl, a methoxy or other alkoxyl group, a methyl or other alkyl group, an aryl group, a carboxylic acid, an amine, an amide, an acetyl group, a guanidino group, or an imidazole. Other contemplated end groups include azide, alkyne, maleimide, aldehyde, hydrazide, hydroxylamine, alkoxyamine, or thiol moieties.

Those of ordinary skill in the art will know of methods and techniques for PEGylating a polymer, for example, by using EDC (1-ethyl-3-(3-dimethylaminopropyl) carbodiimide hydrochloride) and NHS (N-hydroxysuccinimide) to react a polymer to a PEG group terminating in an amine, by ring opening polymerization techniques (ROMP), or the like.

In one embodiment, the molecular weight (or e.g., the ratio of molecular weights of, e.g., different blocks of a copolymer) of the polymers can be optimized for effective treatment as disclosed herein. For example, the molecular weight of a polymer may influence particle degradation rate (such as when the molecular weight of a biodegradable polymer can be adjusted), solubility, water uptake, and drug release kinetics. For example, the molecular weight of the polymer (or e.g., the ratio of molecular weights of, e.g., different blocks of a copolymer) can be adjusted such that the particle biodegrades in the subject being treated within a reasonable period of time (ranging from a few hours to 1-2 weeks, 3-4 weeks, 5-6 weeks, 7-8 weeks, etc.).

A disclosed particle can for example comprise a diblock copolymer of PEG and PL(G)A, wherein for example, the PEG portion may have a number average molecular weight of about 1,000-20,000, e.g., about 2,000-20,000, e.g., about 2 to about 10,000, and the PL(G)A portion may have a number average molecular weight of about 5,000 to about 20,000, or about 5,000-100,000, e.g., about 20,000-70,000, e.g., about 15,000-50,000.

For example, disclosed here is an exemplary nanoparticle that comprises about 10 to about 99 weight percent poly (lactic) acid-poly(ethylene)glycol copolymer or poly(lactic)-co-poly (glycolic) acid-poly(ethylene)glycol copolymer, or about 20 to about 80 weight percent, about 40 to about 80 weight percent, or about 30 to about 50 weight percent, or about 70 to about 90 weight percent poly(lactic) acid-poly(ethylene)glycol copolymer or poly(lactic)-co-poly (glycolic) acid-poly(ethylene)glycol copolymer. Exemplary poly(lactic) acid-poly(ethylene)glycol copolymers can include a number average molecular weight of about 15 to about 20 kDa, or about 10 to about 25 kDa of poly(lactic) acid and a number average molecular weight of about 4 to about 6, or about 2 kDa to about 10 kDa of poly(ethylene) glycol.

In some embodiments, the poly(lactic) acid-poly(ethylene)glycol copolymer may have a poly(lactic) acid number average molecular weight fraction of about 0.6 to about 0.95, in some embodiments between about 0.7 to about 0.9, in some embodiments between about 0.6 to about 0.8, in some embodiments between about 0.7 to about 0.8, in some embodiments between about 0.75 to about 0.85, in some embodiments between about 0.8 to about 0.9, and in some embodiments between about 0.85 to about 0.95. It should be understood that the poly(lactic) acid number average molecular weight fraction may be calculated by dividing the number average molecular weight of the poly(lactic) acid component of the copolymer by the sum of the number average molecular weight of the poly(lactic) acid component and the number average molecular weight of the poly (ethylene)glycol component.

Disclosed nanoparticles may optionally comprise about 1 to about 50 weight percent poly(lactic) acid or poly(lactic) acid-co-poly (glycolic) acid (which does not include PEG), or may optionally comprise about 1 to about 50 weight percent, or about 10 to about 50 weight percent or about 30 to about 50 weight percent poly(lactic) acid or poly(lactic) acid-co-poly (glycolic) acid. For example, poly(lactic) or poly(lactic)-co-poly(glycolic) acid may have a number average molecule weight of about 5 to about 15 kDa, or about 5 to about 12 kDa. Exemplary PLA may have a number average molecular weight of about 5 to about 10 kDa. Exemplary PLGA may have a number average molecular weight of about 8 to about 12 kDa.

A nanoparticle may, in some embodiments, contain about 10 to about 30 weight percent, in some embodiments about 10 to about 25 weight percent, in some embodiments about 10 to about 20 weight percent, in some embodiments about 10 to about 15 weight percent, in some embodiments about 15 to about 20 weight percent, in some embodiments about 15 to about 25 weight percent, in some embodiments about 20 to about 25 weight percent, in some embodiments about 20 to about 30 weight percent, or in some embodiments about 25 to about 30 weight percent of poly(ethylene)glycol, where the poly(ethylene)glycol may be present as a poly (lactic) acid-poly(ethylene)glycol copolymer, poly(lactic)-co-poly (glycolic) acid-poly(ethylene)glycol copolymer, or poly(ethylene)glycol homopolymer. In certain embodiments, the polymers of the nanoparticles can be conjugated to a lipid. The polymer can be, for example, a lipid-terminated PEG.

Preparation of Nanoparticles

Another aspect of this disclosure is directed to systems and methods of making disclosed nanoparticles. In some embodiments, using two or more different polymers (e.g., copolymers, e.g., block copolymers) in different ratios and producing particles from the polymers (e.g., copolymers, e.g., block copolymers), properties of the particles be controlled. For example, a polymer (e.g., copolymer, e.g., block copolymer) may be chosen for its biocompatibility and/or its ability to control immunogenicity of the resultant particle.

In some embodiments, a solvent used in a nanoparticle preparation process (e.g., a nanoprecipitation process or a nanoemulsion process as discussed below) may include a hydrophobic acid, which may confer advantageous properties to the nanoparticles prepared using the process. As discussed above, in some cases, the hydrophobic acid may improve drug loading of disclosed nanoparticles. Furthermore, in some instances, the controlled release properties of disclosed nanoparticles may be improved by the use of the hydrophobic acid. In some cases, the hydrophobic acid may be included in, for example, an organic solution or an aqueous solution used in the process. In one embodiment, the drug is combined with an organic solution and the hydrophobic acid and optionally one or more polymers. The hydrophobic acid concentration in a solution used to dissolve the drug is discussed above and may be, for example, between about 1 weight percent and about 30 weight percent, etc.

In one set of embodiments, the particles are formed by providing a solution comprising one or more polymers, and contacting the solution with a polymer nonsolvent to produce the particle. The solution may be miscible or immiscible with the polymer nonsolvent. For example, a water-miscible liquid such as acetonitrile may contain the polymers, and particles are formed as the acetonitrile is contacted with water, a polymer nonsolvent, e.g., by pouring the acetonitrile into the water at a controlled rate. The polymer contained within the solution, upon contact with the polymer nonsolvent, may then precipitate to form particles such as nanoparticles. Two liquids are said to be "immiscible" or not miscible, with each other when one is not soluble in the other to a level of at least 10% by weight at ambient temperature and pressure. Typically, an organic solution (e.g., dichloromethane, acetonitrile, chloroform, tetrahydrofuran, acetone, formamide, dimethylformamide, pyridines, dioxane, dimethylsulfoxide, etc.) and an aqueous liquid (e.g., water, or water containing dissolved salts or other species, cell or biological media, ethanol, etc.) are immiscible with respect to each other. For example, the first solution may be poured into the second solution (at a suitable rate or speed). In some cases, particles such as nanoparticles may be formed as the first solution contacts the immiscible second liquid, e.g., precipitation of the polymer upon contact causes the polymer to form nanoparticles while the first solution is poured into the second liquid, and in some cases, for example, when the rate of introduction is carefully controlled and kept at a relatively slow rate, nanoparticles may form. The control of such particle formation can be readily optimized by one of ordinary skill in the art using only routine experimentation.

Properties such as surface functionality, surface charge, size, zeta ($\zeta$) potential, hydrophobicity, ability to control immunogenicity, and the like, may be highly controlled using a disclosed process. For instance, a library of particles may be synthesized, and screened to identify the particles having a particular ratio of polymers that allows the particles to have a specific density of moieties present on the surface of the particle. This allows particles having one or more specific properties to be prepared, for example, a specific size and a specific surface density of moieties, without an undue degree of effort. Accordingly, certain embodiments are directed to screening techniques using such libraries, as well as any particles identified using such libraries. In addition, identification may occur by any suitable method. For instance, the identification may be direct or indirect, or proceed quantitatively or qualitatively.

Figure 2A:
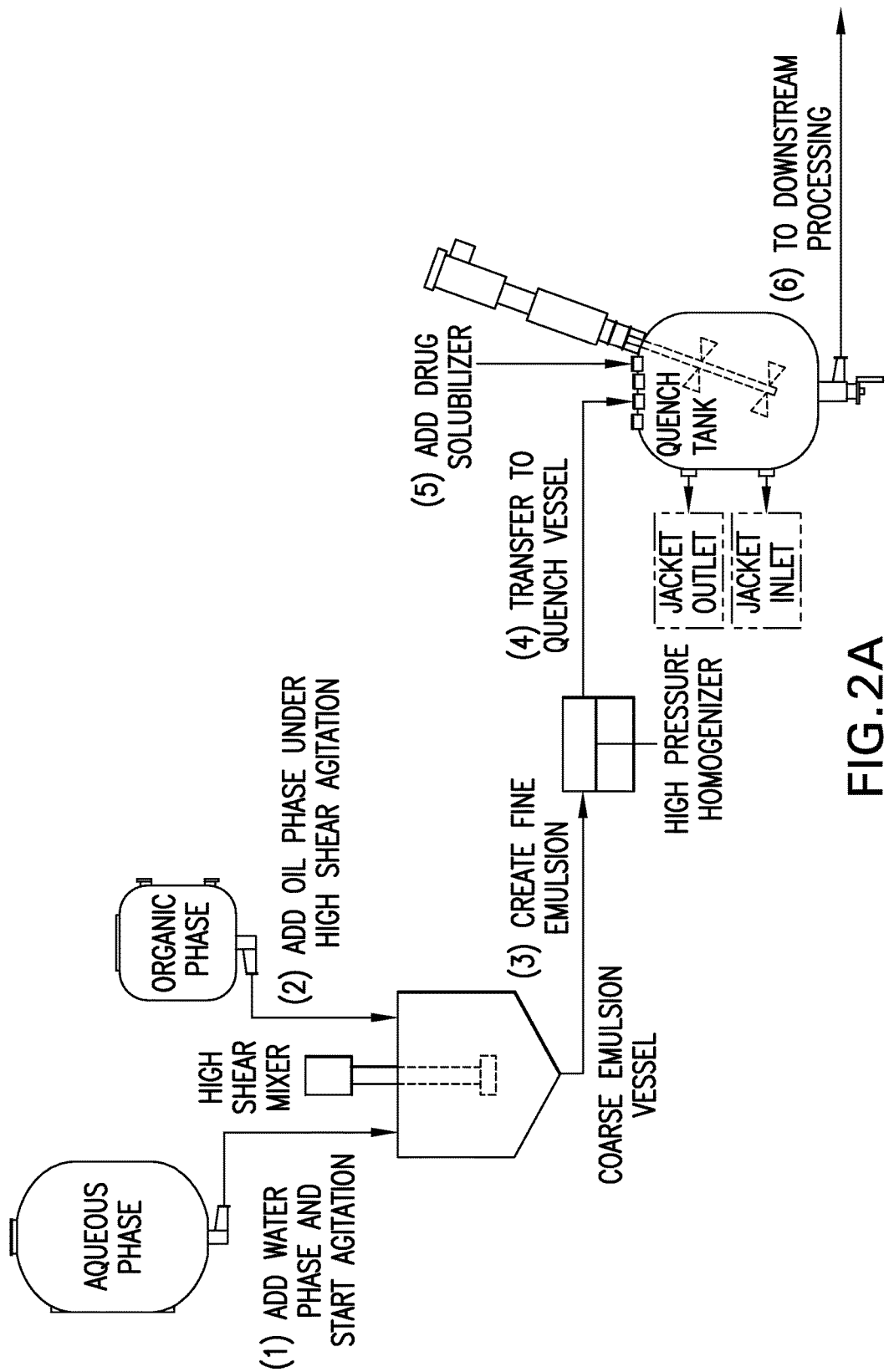
FIGS. 2A and 2B show flow diagrams for a disclosed emulsion process.
Figure 2B:
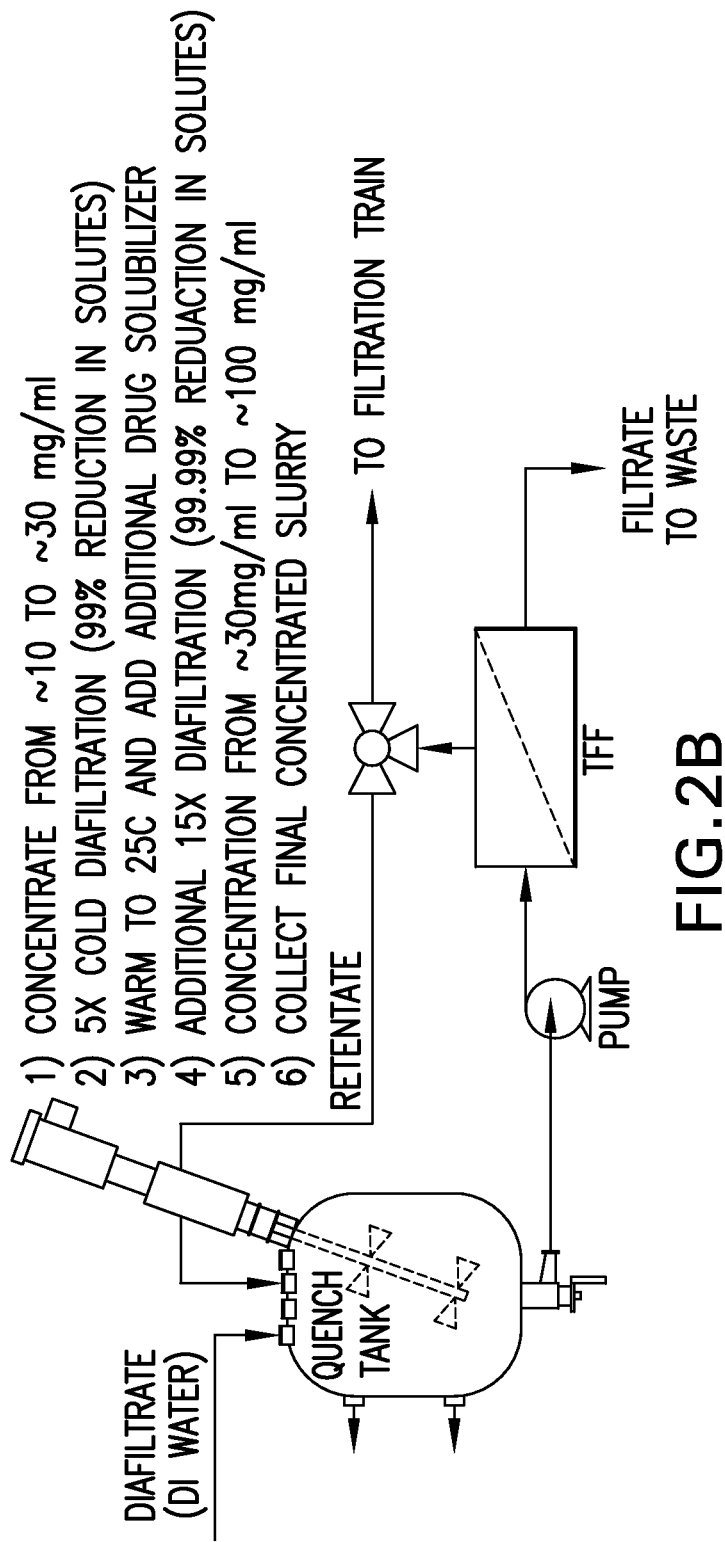

In another embodiment, a nanoemulsion process is provided, such as the process represented in FIGS. 1, 2A, and 2B. For example, the potential therapeutic agent, a hydrophobic acid, a first polymer (for example, a diblock copolymer such as PLA-PEG or PLGA-PEG) and an optional second polymer (e.g., (PL(G)A-PEG or PLA), may be combined with an organic solution to form a first organic phase. Such first organic phase may include about 1 to about 50% weight solids, about 5 to about 50% weight solids, about 5 to about 40% weight solids, about 1 to about 15% weight solids, or about 10 to about 30% weight solids. The first organic phase may be combined with a first aqueous solution to form a second phase. The organic solution can include, for example, toluene, methyl ethyl ketone, acetonitrile, tetrahydrofuran, ethyl acetate, isopropyl alcohol, isopropyl acetate, dimethylformamide, methylene chloride, dichloromethane, chloroform, acetone, benzyl alcohol, Tween 80, Span 80, or the like, and combinations thereof. In an embodiment, the organic phase may include benzyl alcohol, ethyl acetate, and combinations thereof. The second phase can be between about 0.1 and 50 weight %, between about 1 and 50 weight %, between about 5 and 40 weight %, or between about 1 and 15 weight %, solids. The aqueous solution can be water, optionally in combination with one or more of sodium cholate, ethyl acetate, polyvinyl acetate and benzyl alcohol. In some embodiments, the pH of the aqueous phase may be selected based on the $pK_a$ of the protonated agent and/or the $pK_a$ of the hydrophobic acid. For example, in certain embodiments, the agent, when protonated, may have a first $pK_a$, the hydrophobic acid may have a second $pK_a$, and the aqueous phase may have a pH equal to a $pK_a$, unit between the first $pK_a$, and the second $pK_a$. In a particular embodiment, the pH of the aqueous phase may be equal to a $pK_a$, unit that is about equidistant between the the first $pK_a$ and the second $pK_a$.

For example, the oil or organic phase may use a solvent that is only partially miscible with the nonsolvent (water). Therefore, when mixed at a low enough ratio and/or when using water pre-saturated with the organic solvents, the oil phase remains liquid. The oil phase may be emulsified into an aqueous solution and, as liquid droplets, sheared into nanoparticles using, for example, high energy dispersion systems, such as homogenizers or sonicators. The aqueous portion of the emulsion, otherwise known as the "water phase", may be surfactant solution consisting of sodium cholate and pre-saturated with ethyl acetate and benzyl alcohol. In some instances, the organic phase (e.g., first organic phase) may include the potential therapeutic agent. Additionally, in certain embodiments, the aqueous solution (e.g., first aqueous solution) may include the substantially hydrophobic acid. In other embodiments, both the potential therapeutic agent and the substantially hydrophobic acid may be dissolved in the organic phase.

Emulsifying the second phase to form an emulsion phase may be performed, for example, in one or two emulsification steps. For example, a primary emulsion may be prepared, and then emulsified to form a fine emulsion. The primary emulsion can be formed, for example, using simple mixing, a high pressure homogenizer, probe sonicator, stir bar, or a rotor stator homogenizer. The primary emulsion may be formed into a fine emulsion through the use of e.g., probe sonicator or a high pressure homogenizer, e.g., by using 1, 2, 3, or more passes through a homogenizer. For example, when a high pressure homogenizer is used, the pressure used may be about 30 to about 60 psi, about 40 to about 50 psi, about 1000 to about 8000 psi, about 2000 to about 4000 psi, about 4000 to about 8000 psi, or about 4000 to about 5000 psi, e.g., about 2000, 2500, 4000 or 5000 psi.

In some cases, fine emulsion conditions, which can be characterized by a very high surface to volume ratio of the droplets in the emulsion, can be chosen to maximize the solubility of the potential therapeutic agent and hydrophobic acid and form the desired HIP. In certain embodiments, under fine emulsion conditions, equilibration of dissolved components can occur very quickly, i.e., faster than solidification of the nanoparticles. Thus, selecting a HIP based on, e.g., the $pK_a$, difference between the potential therapeutic agent and the hydrophobic acid, or adjusting other parameters such as the pH of the fine emulsion and/or the pH of the quench solution, can have a significant impact on the drug loading and release properties of the nanoparticles by dictating, for example, the formation of a HIP in the nanoparticle as opposed to diffusion of the potential therapeutic agent and/or hydrophobic acid out of the nanoparticle.

In some embodiments, the potential therapeutic agent and the substantially hydrophobic acid may be combined in the second phase prior to emulsifying the second phase. In some instances, the potential therapeutic agent and the substantially hydrophobic acid may form a hydrophobic ion pair prior to emulsifying the second phase. In other embodiments, the potential therapeutic agent and the substantially hydrophobic acid may form a hydrophobic ion pair during emulsification of the second phase. For example, the potential therapeutic agent and the substantially hydrophobic acid may be combined in the second phase substantially concurrently with emulsifying the second phase, e.g., the potential therapeutic agent and the substantially hydrophobic acid may be dissolved in separate solutions (e.g., two substantially immiscible solutions), which are then combined during emulsification. In another example, the potential therapeutic agent and the substantially hydrophobic acid may be dissolved in separate miscible solutions that are then fed into second phase during emulsification.

Either solvent evaporation or dilution may be needed to complete the extraction of the solvent and solidify the particles. For better control over the kinetics of extraction and a more scalable process, a solvent dilution via aqueous quench may be used. For example, the emulsion can be diluted into cold water to a concentration sufficient to dissolve all of the organic solvent to form a quenched phase. In some embodiments, quenching may be performed at least partially at a temperature of about 5° C. or less. For example, water used in the quenching may be at a temperature that is less than room temperature (e.g., about 0 to about 10° C., or about 0 to about 5° C.). In certain embodiments, the quench may be chosen having a pH that is advantageous for quenching the emulsion phase, e.g., by improving the properties of the nanoparticles, such as the release profile, or improving a nanoparticle parameter, such as the drug loading. The pH of the quench may be adjusted by acid or base titration, for example, or by appropriate selection of a buffer. In some embodiments, the pH of the quench may be selected based on the $pK_a$, of the protonoated agent and/or the $pK_a$, of the hydrophobic acid. For example, in certain embodiments, the potential therapeutic agent, when protonated, may have a first $pK_a$, the hydrophobic acid may have a second $pK_a$, and the emulsion phase may be quenched with an aqueous solution having a pH equal to a $pK_a$ unit between the first $pK_a$ and the second $pK_a$. In some embodiments, the resultant quenched phase may also have a pH equal to a $pK_a$, unit between the first $pK_a$, and the second $pK_a$. In a particular embodiment, the pH may be equal to a $pK_a$, unit that is about equidistant between the the first $pK_a$ and the second $pK_a$.

In certain embodiments, HIP formation can occur during or after emulsification, e.g., as a result of equilibrium conditions in the fine emulsion. Without wishing to be bound by any theory, it is believed that organic-soluble counter ions (i.e., the hydrophobic acid) may facilitate diffusion of a potential therapeutic agent into a nanoparticle of an emulsion as a result of HIP formation. Without wishing to be bound by any theory, the HIP may remain in the nanoparticle before solidification of the nanoparticle since the solubility of the HIP in the nanoparticle is higher than the solubility of the HIP in the aqueous phase of the emulsion and/or in the quench. For example, by selecting a pH for the quench that is between the $pK_a$, of the potential therapeutic agent and the $pK_a$, of the hydrophobic acid, formation of ionized agent and hydrophobic acid can be optimized. However, selecting a pH that is too high may tend to cause the hydrophobic acid to diffuse out of the nanoparticle, whereas selecting a pH that is too low may tend to cause the potential therapeutic agent to diffuse out of the nanoparticle.

In some embodiments, the pH of an aqueous solution used in a nanoparticle formulation process (e.g., including, but not limited to, the aqueous phase, the emulsion phase, the quench, and the quenched phase) may be independently selected and may be between about 1 and about 3, in some embodiments between about 2 and about 4, in some embodiments between about 3 and about 5, in some embodiments between about 4 and about 6, in some embodiments between about 5 and about 7, in some embodiments between about 6 and about 8, in some embodiments between about 7 and about 9, and in some embodiments between about 8 and about 10. In certain embodiments, the pH of an aqueous solution used in a nanoparticle formulation process may be between about 3 and about 4, in some embodiments between about 4 and about 5, in some embodiments between about 5 and about 6, in some embodiments between about 6 and about 7, in some embodiments between about 7 and about 8, and in some embodiments between about 8 and about 9.

In some embodiments, not all of the potential therapeutic agent is encapsulated in the particles at this stage, and a drug solubilizer is added to the quenched phase to form a solubilized phase. The drug solubilizer may be for example, Tween 80, Tween 20, polyvinyl pyrrolidone, cyclodextran, sodium dodecyl sulfate, sodium cholate, diethylnitrosamine, sodium acetate, urea, glycerin, propylene glycol, glycofurol, poly(ethylene)glycol, bris(polyoxyethyleneglycol)dodecyl ether, sodium benzoate, sodium salicylate, or combinations thereof. For example, Tween-80 may be added to the quenched nanoparticle suspension to solubilize the free drug and prevent the formation of drug crystals. In some embodiments, a ratio of drug solubilizer to the potential therapeutic agent is about 200:1 to about 10:1, or in some embodiments about 100:1 to about 10:1.

The solubilized phase may be filtered to recover the nanoparticles. For example, ultrafiltration membranes may be used to concentrate the nanoparticle suspension and substantially eliminate organic solvent, free drug (i.e., unencapsulated potential therapeutic agent), drug solubilizer, and other processing aids (surfactants). Exemplary filtration may be performed using a tangential flow filtration system. For example, by using a membrane with a pore size suitable to retain nanoparticles while allowing solutes, micelles, and organic solvent to pass, nanoparticles can be selectively separated. Exemplary membranes with molecular weight cut-offs of about 300-500 kDa (~5-25 nm) may be used.

Diafiltration may be performed using a constant volume approach, meaning the diafiltrate (cold deionized water, e.g., about 0 to about 5° C., or 0 to about 10° C.) may added to the feed suspension at the same rate as the filtrate is removed from the suspension. In some embodiments, filtering may include a first filtering using a first temperature of about 0 to about 5° C., or 0 to about 10° C., and a second temperature of about 20 to about 30° C., or 15 to about 35° C. In some embodiments, filtering may include processing about 1 to about 30, in some cases about 1 to about 15, or in some cases 1 to about 6 diavolumes. For example, filtering may include processing about 1 to about 30, or in some cases about 1 to about 6 diavolumes, at about 0 to about 5° C., and processing at least one diavolume (e.g., about 1 to about 15, about 1 to about 3, or about 1 to about 2 diavolumes) at about 20 to about 30° C. In some embodiments, filtering comprises processing different diavolumes at different distinct temperatures.

After purifying and concentrating the nanoparticle suspension, the particles may be passed through one, two or more sterilizing and/or depth filters, for example, using ~0.2 μm depth pre-filter. For example, a sterile filtration step may involve filtering the potential therapeutic nanoparticles using a filtration train at a controlled rate. In some embodiments, the filtration train may include a depth filter and a sterile filter.

In another embodiment of preparing nanoparticles, an organic phase is formed composed of a mixture of the potential therapeutic agent and polymer (homopolymer and co-polymer). The organic phase is mixed with an aqueous phase at approximately a 1:5 ratio (oil phase:aqueous phase) where the aqueous phase is composed of a surfactant and some dissolved solvent. The primary emulsion is formed by the combination of the two phases under simple mixing or through the use of a rotor stator homogenizer. The primary emulsion is then formed into a fine emulsion through the use of a high pressure homogenizer. The fine emulsion is then quenched by addition to deionized water under mixing. In some embodiments, the quench:emulsion ratio may be about 2:1 to about 40:1, or in some embodiments about 5:1 to about 15:1. In some embodiments, the quench:emulsion ratio is approximately 8.5:1. Then a solution of Tween (e.g., Tween 80) is added to the quench to achieve approximately 2% Tween overall. This serves to dissolve free, unencapsulated potential therapeutic agent. The nanoparticles are then isolated through either centrifugation or ultrafiltration/diafiltration.

It will be appreciated that the amounts of polymer, potential therapeutic agent, and hydrophobic acid that are used in the preparation of the formulation may differ from a final formulation. For example, some of the potential therapeutic agent may not become completely incorporated in a nanoparticle and such free potential therapeutic agent may be e.g., filtered away. For example, in an embodiment, a first organic solution containing about 11 weight percent theoretical loading of potential therapeutic agent in a first organic solution containing about 9% of a first hydrophobic acid (e.g., a fatty acid), a second organic solution containing about 89 weight percent polymer (e.g., the polymer may include PLA-PEG), and an aqueous solution containing about 0.12% of a second hydrophobic acid (e.g., a bile acid) may be used in the preparation of a formulation that results in, e.g., a final nanoparticle comprising about 2 weight percent potential therapeutic agent, about 97.5 weight percent polymer, and about 0.5% total hydrophobic acid. Such processes may provide final nanoparticles suitable for administration to a patient that includes about 1 to about 20 percent by weight potential therapeutic agent, e.g., about 1, about 2, about 3, about 4, about 5, about 8, about 10, or about 15 percent potential therapeutic agent by weight.

Pharmaceutical Formulations

Nanoparticles disclosed herein may be combined with pharmaceutically acceptable carriers to form a pharmaceutical composition, according to another aspect. As would be appreciated by one of skill in this art, the carriers may be chosen based on the route of administration as described below, the location of the target issue, the drug being delivered, the time course of delivery of the drug, etc.

The pharmaceutical compositions can be administered to a patient by any means known in the art including oral and parenteral routes. The term "patient," as used herein, refers to humans as well as non-humans, including, for example, mammals, birds, reptiles, amphibians, and fish. For instance, the non-humans may be mammals (e.g., a rodent, a mouse, a rat, a rabbit, a monkey, a dog, a cat, a primate, or a pig). In certain embodiments parenteral routes are desirable since they avoid contact with the digestive enzymes that are found in the alimentary canal. According to such embodiments, inventive compositions may be administered by injection (e.g., intravenous, subcutaneous or intramuscular, intraperitoneal injection), rectally, vaginally, topically (as by powders, creams, ointments, or drops), or by inhalation (as by sprays).

In a particular embodiment, the nanoparticles are administered to a subject in need thereof systemically, e.g., by IV infusion or injection.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In one embodiment, the inventive conjugate is suspended in a carrier fluid comprising 1% (w/v) sodium carboxymethyl cellulose and 0.1% (v/v) TWEEN™ 80. The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Solid dosage forms for oral administration include capsules, tablets, pills, powders, and granules. In such solid dosage forms, the encapsulated or unencapsulated conjugate is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

It will be appreciated that the exact dosage of a nanoparticle containing the potential therapeutic agent is chosen by the individual physician in view of the patient to be treated, in general, dosage and administration are adjusted to provide an effective amount of the nanoparticle to the patient being treated. As used herein, the "effective amount" of a nanoparticle containing the potential therapeutic agent refers to the amount necessary to elicit the desired biological response. As will be appreciated by those of ordinary skill in this art, the effective amount of a nanoparticle containing the potential therapeutic agent may vary depending on such factors as the desired biological endpoint, the drug to be delivered, the target tissue, the route of administration, etc. For example, the effective amount of a nanoparticle containing the potential therapeutic agent might be the amount that results in a reduction in tumor size by a desired amount over a desired period of time. Additional factors which may be taken into account include the severity of the disease state; age, weight and gender of the patient being treated; diet, time and frequency of administration; drug combinations; reaction sensitivities; and tolerance/response to therapy.

The nanoparticles may be formulated in dosage unit form for ease of administration and uniformity of dosage. The expression "dosage unit form" as used herein refers to a physically discrete unit of nanoparticle appropriate for the patient to be treated. It will be understood, however, that the total daily usage of the compositions will be decided by the attending physician within the scope of sound medical judgment. For any nanoparticle, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. Therapeutic efficacy and toxicity of nanoparticles can be determined by standard pharmaceutical procedures in cell cultures or experimental animals, e.g., $ED_{50}$ (the dose is therapeutically effective in 50% of the population) and $LD_{50}$ (the dose is lethal to 50% of the population). The dose ratio of toxic to therapeutic effects is the therapeutic index, and it can be expressed as the ratio, $LD_{50}/ED_{50}$. Pharmaceutical compositions which exhibit large therapeutic indices may be useful in some embodiments. The data obtained from cell culture assays and animal studies can be used in formulating a range of dosage for human use.

In an embodiment, compositions disclosed herein may comprise less than about 10 ppm of palladium, or less than about 8 ppm, or less than about 6 ppm of palladium. For example, provided here is a composition that comprises nanoparticles wherein the composition has less than about 10 ppm of palladium.

In some embodiments, a composition suitable for freezing is contemplated, including nanoparticles disclosed herein and a solution suitable for freezing, e.g., a sugar such as a mono, di, or poly saccharide, e.g., sucrose and/or a trehalose, and/or a salt and/or a cyclodextrin solution is added to the nanoparticle suspension. The sugar (e.g., sucrose or trehalose) may act, e.g., as a cryoprotectant to prevent the particles from aggregating upon freezing. For example, provided herein is a nanoparticle formulation comprising a plurality of disclosed nanoparticles, sucrose, an ionic halide, and water; wherein the nanoparticles/sucrose/water/ionic halide is about 3-40%/10-40%/20-95%/0.1-10% (w/w/w/w) or about 5-10%/10-15%/80-90%/1-10% (w/w/w/w). For example, such solution may include nanoparticles as disclosed herein, about 5% to about 20% by weight sucrose and an ionic halide such as sodium chloride, in a concentration of about 10-100 mM. In another example, provided herein is a nanoparticle formulation comprising a plurality of disclosed nanoparticles, trehalose, cyclodextrin, and water; wherein the nanoparticles/trehalose/water/cyclodextrin is about 3-40%/1-25%/20-95%/1-25% (w/w/w/w) or about 5-10%/1-25%/80-90%/10-15% (w/w/w/w).

For example, a contemplated solution may include nanoparticles as disclosed herein, about 1% to about 25% by weight of a disaccharide such as trehalose or sucrose (e.g., about 5% to about 25% trehalose or sucrose, e.g. about 10% trehalose or sucrose, or about 15% trehalose or sucrose, e.g. about 5% sucrose) by weight) and a cyclodextrin such as β-cyclodextrin, in a concentration of about 1% to about 25% by weight (e.g. about 5% to about 20%, e.g. 10% or about 20% by weight, or about 15% to about 20% by weight cyclodextrin). Contemplated formulations may include a plurality of disclosed nanoparticles (e.g. nanoparticles having PLA-PEG and an active agent), and about 2% to about 15 wt % (or about 4% to about 6 wt %, e.g. about 5 wt %) sucrose and about 5 wt % to about 20% (e.g. about 7% wt percent to about 12 wt %, e.g. about 10 wt %) of a cyclodextrin, e.g., HPbCD).

The present disclosure relates in part to lyophilized pharmaceutical compositions that, when reconstituted, have a minimal amount of large aggregates. Such large aggregates may have a size greater than about 0.5 μm, greater than about 1 μm, or greater than about 10 μm, and can be undesirable in a reconstituted solution. Aggregate sizes can be measured using a variety of techniques including those indicated in the U.S. Pharmacopeia at 32 <788>, hereby incorporated by reference. The tests outlined in USP 32 <788> include a light obscuration particle count test, microscopic particle count test, laser diffraction, and single particle optical sensing. In one embodiment, the particle size in a given sample is measured using laser diffraction and/or single particle optical sensing.

The USP 32 <788> by light obscuration particle count test sets forth guidelines for sampling particle sizes in a suspension. For solutions with less than or equal to 100 mL, the preparation complies with the test if the average number of particles present does not exceed 6000 per container that are ≥10 μm and 600 per container that are ≥25 μm.

As outlined in USP 32 <788>, the microscopic particle count test sets forth guidelines for determining particle amounts using a binocular microscope adjusted to 100±10× magnification having an ocular micrometer. An ocular micrometer is a circular diameter graticule that consists of a circle divided into quadrants with black reference circles denoting 10 μm and 25 μm when viewed at 100× magnification. A linear scale is provided below the graticule. The number of particles with reference to 10 μm and 25 μm are visually tallied. For solutions with less than or equal to 100 mL, the preparation complies with the test if the average number of particles present does not exceed 3000 per container that are ≥10 μm and 300 per container that are ≥25 μm.

In some embodiments, a 10 mL aqueous sample of a disclosed composition upon reconstitution comprises less than 600 particles per ml having a size greater than or equal to 10 microns; and/or less than 60 particles per ml having a size greater than or equal to 25 microns.

Dynamic light scattering (DLS) may be used to measure particle size, but it relies on Brownian motion so the technique may not detect some larger particles. Laser diffraction relies on differences in the index of refraction between the particle and the suspension media. The technique is capable of detecting particles at the sub-micron to millimeter range. Relatively small (e.g., about 1-5 weight %) amounts of larger particles can be determined in nanoparticle suspensions. Single particle optical sensing (SPOS) uses light obscuration of dilute suspensions to count individual particles of about 0.5 μm. By knowing the particle concentration of the measured sample, the weight percentage of aggregates or the aggregate concentration (particles/mL) can be calculated.

Formation of aggregates can occur during lyophilization due to the dehydration of the surface of the particles. This dehydration can be avoided by using lyoprotectants, such as disaccharides, in the suspension before lyophilization. Suitable disaccharides include sucrose, lactulose, lactose, maltose, trehalose, or cellobiose, and/or mixtures thereof. Other contemplated disaccharides include kojibiose, nigerose, isomaltose, β,β-trehalose, α,β-trehalose, sophorose, laminaribiose, gentiobiose, turanose, maltulose, palatinose, gentiobiulose, mannobiase, melibiose, melibiulose, rutinose, rutinulose, and xylobiose. Reconstitution shows equivalent DLS size distributions when compared to the starting suspension. However, laser diffraction can detect particles of >10 μm in size in some reconstituted solutions. Further, SPOS also may detect >10 μm sized particles at a concentration above that of the FDA guidelines ($10^4$-$10^5$ particles/mL for >10 μm particles).

In some embodiments, one or more ionic halide salts may be used as an additional lyoprotectant to a sugar, such as sucrose, trehalose or mixtures thereof. Sugars may include disaccharides, monosaccharides, trisaccharides, and/or polysaccharides, and may include other excipients, e.g. glycerol and/or surfactants. Optionally, a cyclodextrin may be included as an additional lyoprotectant. The cyclodextrin may be added in place of the ionic halide salt. Alternatively, the cyclodextrin may be added in addition to the ionic halide salt.

Suitable ionic halide salts may include sodium chloride, calcium chloride, zinc chloride, or mixtures thereof. Additional suitable ionic halide salts include potassium chloride, magnesium chloride, ammonium chloride, sodium bromide, calcium bromide, zinc bromide, potassium bromide, magnesium bromide, ammonium bromide, sodium iodide, calcium iodide, zinc iodide, potassium iodide, magnesium iodide, or ammonium iodide, and/or mixtures thereof. In one embodiment, about 1 to about 15 weight percent sucrose may be used with an ionic halide salt. In one embodiment, the lyophilized pharmaceutical composition may comprise about 10 to about 100 mM sodium chloride. In another embodiment, the lyophilized pharmaceutical composition may comprise about 100 to about 500 mM of divalent ionic chloride salt, such as calcium chloride or zinc chloride. In yet another embodiment, the suspension to be lyophilized may further comprise a cyclodextrin, for example, about 1 to about 25 weight percent of cyclodextrin may be used.

A suitable cyclodextrin may include α-cyclodextrin, β-cyclodextrin, γ-cyclodextrin, or mixtures thereof. Exemplary cyclodextrins contemplated for use in the compositions disclosed herein include hydroxypropyl-β-cyclodextrin (HPbCD), hydroxyethyl-β-cyclodextrin, sulfobutylether-β-cyclodextrin, methyl-β-cyclodextrin, dimethyl-β-cyclodextrin, carboxymethyl-β-cyclodextrin, carboxymethyl ethyl-β-cyclodextrin, diethyl-β-cyclodextrin, tri-O-alkyl-β-cyclodextrin, glocosyl-β-cyclodextrin, and maltosyl-β-cyclodextrin. In one embodiment, about 1 to about 25 weight percent trehalose (e.g. about 10% to about 15%, e.g. 5 to about 20% by weight) may be used with cyclodextrin. In one embodiment, the lyophilized pharmaceutical composition may comprise about 1 to about 25 weight percent β-cyclodextrin. An exemplary composition may comprise nanoparticles comprising PLA-PEG, an active agent, about 4% to about 6% (e.g. about 5% wt percent) sucrose, and about 8 to about 12 weight percent (e.g. about 10 wt. %) HPbCD.

In one aspect, a lyophilized pharmaceutical composition is provided comprising disclosed nanoparticles, wherein upon reconstitution of the lyophilized pharmaceutical composition at a nanoparticle concentration of about 50 mg/mL, in less than or about 100 mL of an aqueous medium, the reconstituted composition suitable for parenteral administration comprises less than 6000, such as less than 3000, microparticles of greater than or equal to 10 microns; and/or less than 600, such as less than 300, microparticles of greater than or equal to 25 microns.

The number of microparticles can be determined by means such as the USP 32 <788> by light obscuration particle count test, the USP 32 <788> by microscopic particle count test, laser diffraction, and single particle optical sensing.

In an aspect, a pharmaceutical composition suitable for parenteral use upon reconstitution is provided comprising a plurality of polymeric nanoparticles each comprising a copolymer having a hydrophobic polymer segment and a hydrophilic polymer segment; an active agent; a sugar; and a cyclodextrin.

For example, the copolymer may be poly(lactic) acid-block-poly(ethylene)glycol copolymer. Upon reconstitution, a 100 mL aqueous sample may comprise less than 6000 particles having a size greater than or equal to 10 microns; and less than 600 particles having a size greater than or equal to 25 microns.

The step of adding a disaccharide and an ionic halide salt may comprise adding about 5 to about 15 weight percent sucrose or about 5 to about 20 weight percent trehalose (e.g., about 10 to about 20 weight percent trehalose), and about 10 to about 500 mM ionic halide salt. The ionic halide salt may be selected from sodium chloride, calcium chloride, and zinc chloride, or mixtures thereof. In an embodiment, about 1 to about 25 weight percent cyclodextrin is also added.

In another embodiment, the step of adding a disaccharide and a cyclodextrin may comprise adding about 5 to about 15 weight percent sucrose or about 5 to about 20 weight percent trehalose (e.g., about 10 to about 20 weight percent trehalose), and about 1 to about 25 weight percent cyclodextrin. In an embodiment, about 10 to about 15 weight percent cyclodextrin is added. The cyclodextrin may be selected from α-cyclodextrin, β-cyclodextrin, γ-cyclodextrin, or mixtures thereof.

In another aspect, a method of preventing substantial aggregation of particles in a pharmaceutical nanoparticle composition is provided comprising adding a sugar and a salt to the lyophilized formulation to prevent aggregation of the nanoparticles upon reconstitution. In an embodiment, a cyclodextrin is also added to the lyophilized formulation. In yet another aspect, a method of preventing substantial aggregation of particles in a pharmaceutical nanoparticle composition is provided comprising adding a sugar and a cyclodextrin to the lyophilized formulation to prevent aggregation of the nanoparticles upon reconstitution.

A contemplated lyophilized composition may have a polymeric nanoparticle concentration of greater than about 40 mg/mL. The formulation suitable for parenteral administration may have less than about 600 particles having a size greater than 10 microns in a 10 mL dose. Lyophilizing may comprise freezing the composition at a temperature of greater than about −40° C., or e.g. less than about −30° C., forming a frozen composition; and drying the frozen composition to form the lyophilized composition. The step of drying may occur at about 50 mTorr at a temperature of about −25 to about −34° C., or about −30 to about −34° C.

Methods of Treatment

In some embodiments, contemplated nanoparticles may be used to treat, alleviate, ameliorate, relieve, delay onset of, inhibit progression of, reduce severity of, and/or reduce incidence of one or more symptoms or features of a disease, disorder, and/or condition. In some embodiments, contemplated nanoparticles may be used to treat solid tumors, e.g., cancer and/or cancer cells.

The term "cancer" includes pre-malignant as well as malignant cancers. Cancers include, but are not limited to, blood (e.g., chronic myelogenous leukemia, chronic myelomonocytic leukemia, Philadelphia chromosome positive acute lymphoblastic leukemia, mantle cell lymphoma), prostate, gastric cancer, colorectal cancer, skin cancer, e.g., melanomas or basal cell carcinomas, lung cancer (e.g., non-small cell lung cancer), breast cancer, cancers of the head and neck, bronchus cancer, pancreatic cancer, urinary bladder cancer, brain or central nervous system cancer, peripheral nervous system cancer, esophageal cancer, cancer of the oral cavity or pharynx, liver cancer (e.g., hepatocellular carcinoma), kidney cancer (e.g., renal cell carcinoma), testicular cancer, biliary tract cancer, small bowel or appendix cancer, gastrointestinal stromal tumor, salivary gland cancer, thyroid gland cancer, adrenal gland cancer, osteosarcoma, chondrosarcoma, cancer of hematological tissues, and the like. "Cancer cells" can be in the form of a tumor (i.e., a solid tumor), exist alone within a subject (e.g., leukemia cells), or be cell lines derived from a cancer.

Cancer can be associated with a variety of physical symptoms. Symptoms of cancer generally depend on the type and location of the tumor. For example, lung cancer can cause coughing, shortness of breath, and chest pain, while colon cancer often causes diarrhea, constipation, and blood in the stool. However, to give but a few examples, the following symptoms are often generally associated with many cancers: fever, chills, night sweats, cough, dyspnea, weight loss, loss of appetite, anorexia, nausea, vomiting, diarrhea, anemia, jaundice, hepatomegaly, hemoptysis, fatigue, malaise, cognitive dysfunction, depression, hormonal disturbances, neutropenia, pain, non-healing sores, enlarged lymph nodes, peripheral neuropathy, and sexual dysfunction.

In one aspect, a method for the treatment of cancer is provided. In some embodiments, the treatment of cancer comprises administering a therapeutically effective amount of inventive particles to a subject in need thereof, in such amounts and for such time as is necessary to achieve the desired result. In certain embodiments, a "therapeutically effective amount" of an inventive particle is that amount effective for treating, alleviating, ameliorating, relieving, delaying onset of, inhibiting progression of, reducing severity of, and/or reducing incidence of one or more symptoms or features of cancer.

In one aspect, a method for administering inventive compositions to a subject suffering from cancer is provided. In some embodiments, nanoparticles may be administered to a subject in such amounts and for such time as is necessary to achieve the desired result (i.e., treatment of cancer). In certain embodiments, a "therapeutically effective amount" of a contemplated nanoparticle is that amount effective for treating, alleviating, ameliorating, relieving, delaying onset of, inhibiting progression of, reducing severity of, and/or reducing incidence of one or more symptoms or features of cancer.

Inventive therapeutic protocols involve administering a therapeutically effective amount of a contemplated nanoparticle to a healthy individual (i.e., a subject who does not display any symptoms of cancer and/or who has not been diagnosed with cancer). For example, healthy individuals may be "immunized" with a contemplated nanoparticle prior to development of cancer and/or onset of symptoms of cancer; at risk individuals (e.g., patients who have a family history of cancer; patients carrying one or more genetic mutations associated with development of cancer; patients having a genetic polymorphism associated with development of cancer; patients infected by a virus associated with development of cancer; patients with habits and/or lifestyles associated with development of cancer; etc.) can be treated substantially contemporaneously with (e.g., within 48 hours, within 24 hours, or within 12 hours of) the onset of symptoms of cancer. Of course, individuals known to have cancer may receive inventive treatment at any time.

In other embodiments, disclosed nanoparticles can be used to inhibit the growth of cancer cells, e.g., lung cancer cells. As used herein, the term "inhibits growth of cancer cells" or "inhibiting growth of cancer cells" refers to any slowing of the rate of cancer cell proliferation and/or migration, arrest of cancer cell proliferation and/or migration, or killing of cancer cells, such that the rate of cancer cell growth is reduced in comparison with the observed or predicted rate of growth of an untreated control cancer cell. The term "inhibits growth" can also refer to a reduction in size or disappearance of a cancer cell or tumor, as well as to a reduction in its metastatic potential. Preferably, such an inhibition at the cellular level may reduce the size, deter the growth, reduce the aggressiveness, or prevent or inhibit metastasis of a cancer in a patient. Those skilled in the art can readily determine, by any of a variety of suitable indicia, whether cancer cell growth is inhibited.

Inhibition of cancer cell growth may be evidenced, for example, by arrest of cancer cells in a particular phase of the cell cycle, e.g., arrest at the G2/M phase of the cell cycle. Inhibition of cancer cell growth can also be evidenced by direct or indirect measurement of cancer cell or tumor size. In human cancer patients, such measurements generally are made using well known imaging methods such as magnetic resonance imaging, computerized axial tomography and X-rays. Cancer cell growth can also be determined indirectly, such as by determining the levels of circulating carcinoembryonic antigen, prostate specific antigen or other cancer-specific antigens that are correlated with cancer cell growth. Inhibition of cancer growth is also generally correlated with prolonged survival and/or increased health and well-being of the subject.

In some embodiments, a method for reducing hyperglycemia in a subject being treated for cancer is provided comprising administering a therapeutically effective amount of contemplated particles to a subject in need thereof, wherein the contemplated particles comprise a kinase inhibitor (e.g., COMPOUND A). In certain embodiments, a "therapeutically effective amount" of an inventive particle is that amount effective for treating, alleviating, ameliorating, relieving, delaying onset of, inhibiting progression of, reducing severity of, and/or reducing incidence of hyperglycemia.

In some embodiments, the fasting blood glucose level in a hyperglycemic subject being treated for cancer may be reduced to a level substantially the same as the fasting blood glucose level in the subject prior to be being treated for cancer. In other embodiments, the fasting blood glucose level of a hyperglycemic subject being treated for cancer may be reduced by between about 10% and about 80%, between about 20% and about 80%, between about 30% and about 80%, between about 40% and about 80%, between about 50% and about 80%, or between about 60% and about 80% from a hyperglycemic fasting blood glucose level in the subject. In other embodiments, the blood glucose level of a hyperglycemic subject being treated for cancer may be reduced by at least about 10%, at least about 20%, at least about 30%, at least about 40%, at least about 50%, at least about 60%, at least about 70%, or at least about 80% from a hyperglycemic fasting blood glucose level in the subject.

In another embodiment, a method for preventing hyperglycemia in a subject being treated for cancer is provided comprising administering a therapeutically effective amount of contemplated particles to a subject in need thereof, wherein the contemplated particles comprise a kinase inhibitor (e.g., COMPOUND A).

In some embodiments, the fasting blood glucose level of a hyperglycemic human patient may be above about 126 mg/dL, above about 150 mg/dL, above about 175 mg/dL, or above about 200 mg/dL.

In another embodiment, a method for maintaining a fasting blood glucose level of between about 70 mg/dL and about 126 mg/dL in a subject being treated for cancer is provided comprising administering a therapeutically effective amount of contemplated particles to a subject in need thereof, wherein the contemplated particles comprise a kinase inhibitor (e.g., COMPOUND A).

Also provided herein are methods of administering to a patient a nanoparticle disclosed herein including an active agent, wherein, upon administration to a patient, such nanoparticles substantially reduces the volume of distribution and/or substantially reduces free $C_{max}$, as compared to administration of the agent alone (i.e., not as a disclosed nanoparticle).

EXAMPLES

The invention now being generally described, it will be more readily understood by reference to the following examples which are included merely for purposes of illustration of certain aspects and embodiments, and are not intended to limit the invention in any way.

Example 1: Preparation of Polymeric Nanoparticles Containing 8-[4-(1-amino-cyclobutyl)phenyl]-9-phenyl-2H-[1,2,4]-triazolo-[3,4-f][1,6]-naphthyridin-3-one dihydrochloride Using a Nanoemulsion Process This example demonstrates procedures for preparing nanoparticles containing 8-[4-(1-amino-cyclobutyl)phenyl]-9-phenyl-2H-[1,2,4]-triazolo-[3,4-f][1,6]-naphthyridin-3-one.

Cholic Acid (Cholate) Nanoparticle Preparation Procedure
1. Preparation of drug/polymer solution
   1.1 3% trifluoroacetic acid solution in benzyl alcohol containing 7.5% water
      1.1.1 To 250 mL glass bottle add 185 g of benzyl alcohol.
      1.1.2 Add 15 g of deionized water.
      1.1.3 Mix by vortexing to give benzyl alcohol containing 7.5% water.
      1.1.4 To 250 mL glass bottle add 194 g of benzyl alcohol containing 7.5% water.
      1.1.5 Add 6 g of trifluoroacetic acid.
      1.1.6 Mix by vortexing.
   1.2 COMPOUND A solution in 3% trifluoroacetic acid solution in benzyl alcohol containing 7.5% water
      1.2.1 To 150 mL glass bottle, add 2.5 g of COMPOUND A.
      1.2.2 Add 25.096 g of 3% trifluoroacetic acid solution in benzyl alcohol containing 7.5% water.
      1.2.3 Vortex until drug is dissolved completely.
   1.3 Polymer solution in ethyl acetate
      1.3.1 To 100 mL glass bottle, add 10 g of polymer PLA-PEG.
      1.3.2 Add 58.558 g of ethylacetate.
      1.3.3 Vortex until polymer is dissolved completely.
   1.4 Right before formulation, add polymer solution to COMPOUND A solution, and vortex until homogenous clear solution is observed.
2. Preparation of Aqueous Solution:
   0.93% Sodium Cholate, 4% Benzyl Alcohol in Water
   2.1 To 2 L bottle add 18.6 g sodium cholate and 1901.4 g of deionized water and mix on stir plate until dissolved.
   2.2 Add 80 g of benzyl alcohol to sodium cholate/water and mix on stir plate until dissolved.
3. Formation of emulsion. Ratio of Aqueous phase to Oil phase is 5:1
   3.1 Pour organic phase into aqueous solution and homogenize using hand homogenizer for 10 seconds at room temperature to form course emulsion
   3.2 Feed solution through high pressure homogenizer (110S) with pressure set at 9320 psi on gauge for 1 pass to form nanoemulsion.
4. Formation of nanoparticles
   Pour emulsion into Quench (deionized water) at <5 C while stirring on stir plate. Ratio of Quench to Emulsion is 10:1
5. Add 35% (w/w) Tween 80 in water to quench at weight ratio of 150:1 Tween 80 to drug.
6. Concentrate nanoparticles through TFF
   6.1 Concentrate quench on TFF with 300 kDa Pall cassette (4 membranes) to ~1000 mL.
   6.2 Diafilter ~20 diavolumes (20 liter) of cold deionized water. Bring volume down to minimal volume
   6.3 Add ~500 mL of cold water to vessel and pump through membrane to rinse.
   6.4 Collect material in glass bottle, ~800 mL
   6.5 Further concentrate the collection in smaller TFF with 300 kDa Pall cassette (2 membranes), and bring volume down to minimal volume
   6.6 Collect material in glass bottle, ~300 mL.
7. Determination of solids concentration of final slurry:
   7.1 To tared 20 mL scintillation vial add a volume of final slurry and dry under vacuum on lyo/oven.
   7.2 Determine weight of nanoparticles in the volume of slurry dried down.
8. Add concentrated sucrose to final slurry sample to attain 30% sucrose.
9. Freeze remaining sample of slurry with sucrose.

Oleic Acid (Oleate) Nanoparticle Preparation Procedure
1. Preparation of drug/polymer solution:
   1.1 5% oleic acid solution in benzyl alcohol
      1.1.1 To 500 mL glass bottle add 491.81 g of benzyl alcohol.
      1.1.2 Add 25.885 g of oleic acid.
      1.1.3 Mix by vortexing.
   1.2 COMPOUND A solution in 5% oleic acid solution in benzyl alcohol
      1.2.1 To 2 L glass bottle, add 12 g of COMPOUND A.
      1.2.2 Add 199.40 g of 5% oleic acid solution in benzyl.
      1.2.3 Vortex until drug is dissolved completely.
   1.3 Polymer solution in ethyl acetate
      1.3.1 To 1 L glass bottle, add 28 g of polymer PLA-PEG.
      1.3.2 Add 773.26 g of ethylacetate.
      1.3.3 Vortex until polymer is dissolved completely.
   1.4 Right before formulation, add polymer solution to COMPOUND A solution, and vortex until homogenous clear solution is observed.
2. Preparation of Aqueous Solution:
   0.1% Sodium Cholate, 4% Benzyl Alcohol in Water
   2.1 To 10 L bottle add 10 g sodium cholate and 9590 g of deionized water and mix on stir plate until dissolved.
   2.2 Add 400 g of benzyl alcohol to sodium cholate/water and mix on stir plate until dissolved.
3. Formation of emulsion. Ratio of Aqueous phase to Oil phase is 5:1.
   3.1 Pour organic phase into aqueous solution and homogenize using hand homogenizer for 10 seconds at room temperature to form course emulsion.
   3.2 Feed solution through high pressure homogenizer (110S) with pressure set at 10718 psi on gauge for 1 pass to form nanoemulsion.

4. Formation of nanoparticles:
   Pour emulsion into Quench (deionized water) at <5 C while stirring on stir plate. Ratio of Quench to Emulsion is 10:1.
5. Add 35% (w/w) Tween 80 in water to quench at weight ratio of 150:1 Tween 80 to drug.
6. Concentrate nanoparticles through TFF:
   6.1 Concentrate quench on TFF with 300 kDa Pall cassette (4 membranes) to ~1000 mL.
   6.2 Diafilter ~20 diavolumes (20 liter) of cold deionized water. Bring volume down to minimal volume.
   6.3 Add ~500 mL of cold water to vessel and pump through membrane to rinse.
   6.4 Collect material in glass bottle, ~800 mL.
   6.5 Further concentrate the collection in smaller TFF with 300 kDa Pall cassette (2 membranes), and bring volume down to minimal volume.
   6.6 Collect material in glass bottle, ~300 mL.
7. Determination of solids concentration of final slurry:
   7.1 To tared 20 mL scintillation vial add a volume of final slurry and dry under vacuum on lyo/oven.
   7.2 Determine weight of nanoparticles in the volume of slurry dried down.
8. Add concentrated sucrose to final slurry sample to attain 30% sucrose.
9. Freeze remaining sample of slurry with sucrose.

Example 2: Characterization of Polymeric Nanoparticles Containing 8-[4-(1-amino-cyclobutyl)phenyl]-9-phenyl-2H-[1,2,4]-triazolo-[3,4-f][1,6]-naphthyridin-3-one This example demonstrates that co-encapsulation with hydrophobic counterions such as cholate and oleate greatly improved drug loading (i.e., from ~3% to up to ~15% drug loading). The release of agent from nanoparticles was substantially slower when formulated as a hydrophobic ion pair compared to the control formulation.

Control Formulations

Control formulations were made as plain nanoparticles ("NPs") without any counterions. NPs were prepared using PLA-PEG polymer matrix (16 kDa PLA/5 kDa PEG) ("16/5 PLA-PEG") with no additional excipients.

The agent was dissolved in benzyl alcohol ("BA") or BA/water to form the drug solution, and polymer solution in ethyl acetate ("EA") was poured into the drug solution right before adding to aqueous for homogenization. This control formulation results in nanoparticles with high burst (~20%), and fast release (>70% at 4 hrs). (See FIG. 4) These results are not unusual for APIs with relatively low MW (e.g., <600 kDa) and/or lesser hydrophobicity (e.g., log P<3).

TABLE 2

Control nanoparticle formulation.

| Lot # | Drug theoretical loading | Solid con | Loading % | size (nm) (polydispersity) |
|---|---|---|---|---|
| 16/5 PLA-PEG, 7.5% water in BA only | 20 | 7% | 5.2 | 119 (0.22) |

Cholic Acid and Oleic Acid Formulations

Cholic acid and oleic acid formulations were made according to the procedure in Example 1 using various amounts of cholic acid or oleic acid in the organic phase as shown in Table 3. NPs were prepared using 16/5 PLA-PEG.

TABLE 3

Nanoparticle formulations.

| Lot # | Counter ion | Drug theoretical loading | Solid con (%) | Loading | size (nm) | Acid/drug molar ratio | drug con (mg/ml) in the final with 30% sucrose | % SC |
|---|---|---|---|---|---|---|---|---|
| 220-10-D: 16/5, 3% TFA in BA, 30/70 BA/EA | Cholic acid | 20 | 13 | 7.94% | 106.1 | ? | 7.91 | 0.93% SC, 1@40 psi |
| 146-30-C3: 16/5., 5% oleic acid in BA, 20.5/79.5 BA/EA | Oleic acid | 30 | 3.95 | 6.06% | 124.6 | 1.2 | 5.73 | 0.1% SC, 1@46 psi |

Particle sizes of formulations were controlled within the range of 100-130 nm. Drug loadings were all above 5%. Cholic acid was encapsulated into NPs as counter ion of COMPOUND A, using TFA in organic phase and sodium cholate in aqueous phase. Oleic acid was encapsulated into NPs at 1.2 molar ratio of acid/drug by direct addition to the organic phase.

Figure 3:
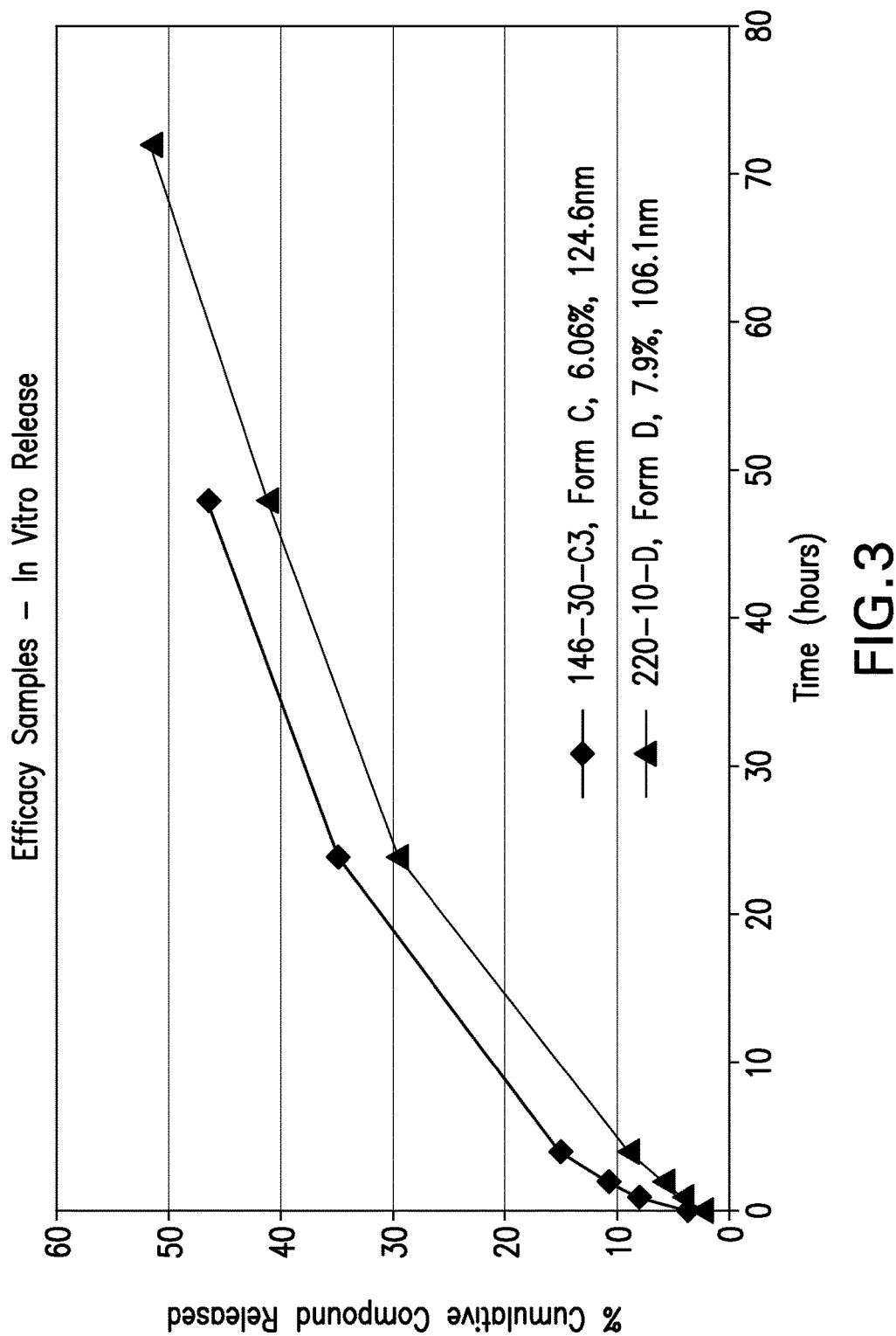
FIG. 3 depicts an in vitro release profile for control therapeutic nanoparticle formulations.

Example 3: Release Properties of Polymeric Nanoparticles Containing 8-[4-(1-amino-cyclobutyl)phenyl]-9-phenyl-2H-[1,2,4]-triazolo-[3,4-f][1,6]-naphthyridin-3-one In vitro release profiles of the nanoparticles prepared in Example 1 are plotted in FIG. 3. Nanoparticles (NPs) prepared using cholic acid as counter ion (lot 220-10-D) release drug slightly slower than NPs prepared using oleic acid as counter ion (lot 146-30-C3). At 24 hours, about 30% and 35% release were measured for lot 220-10-D and lot 146-30-C3, respectively.

Figure 4:
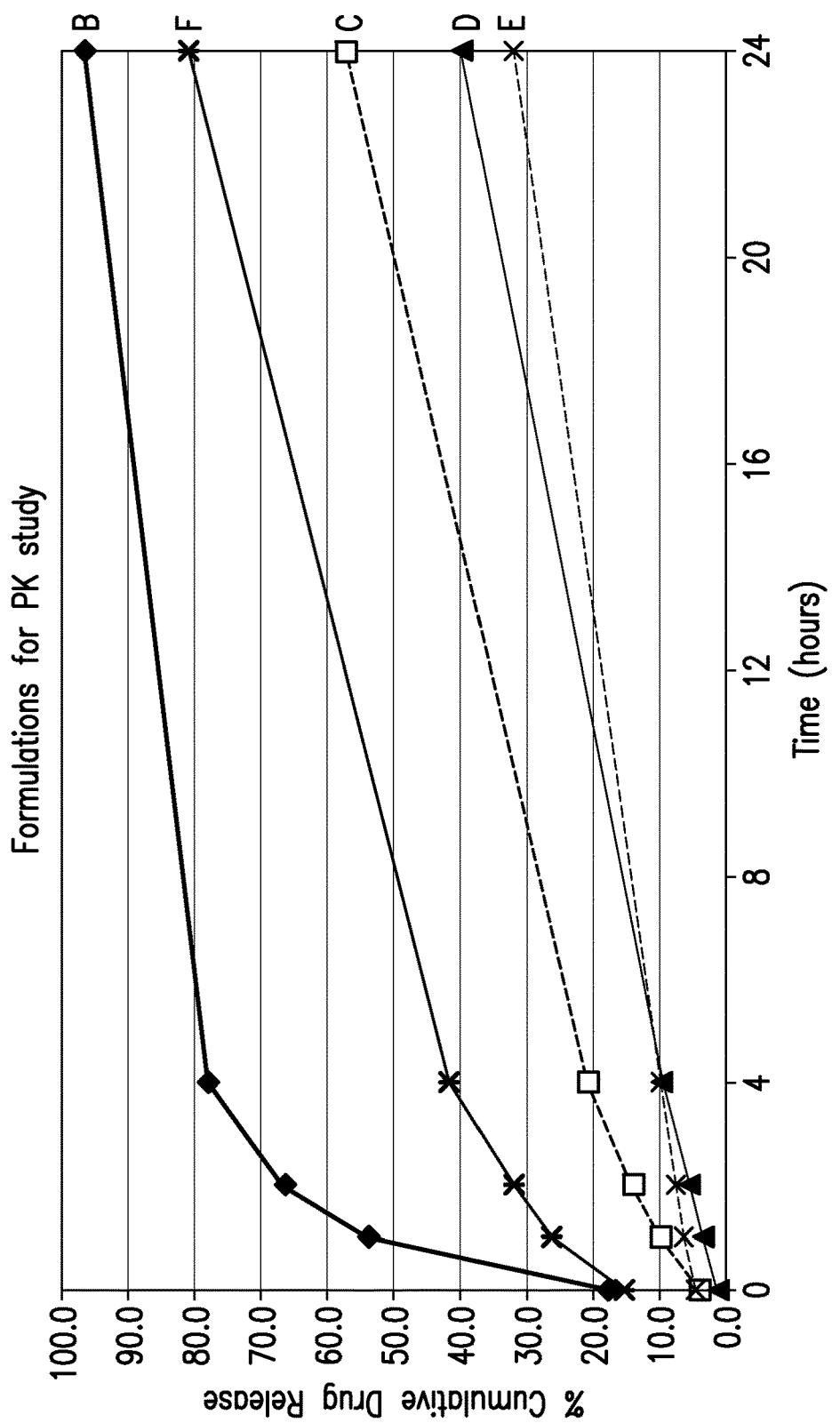
FIG. 4 depicts in vitro release profiles for cholic acid counterion or oleic acid counterion nanoparticle formulations versus a control therapeutic nanoparticle formulation (NP-B).

Example 4: Pharmacokinetic (PK) and Pharmacodynamic (PD) Properties of Polymeric Nanoparticles Containing 8-[4-(1-amino-cyclobutyl)phenyl]-9-phenyl-2H-[1,2,4]-triazolo-[3,4-f][1,6]-naphthyridin-3-one Nanoparticles (NPs) were prepared using analogously to the methods described in Example 1. Table 4 shows the properties for NP formulations and FIG. 4 shows the in vitro release profiles. Formulation NP-B (control) utilized a blend of 16/5 and 47/5 copolymers with no acid to evaluate independently the influence of polymer molecular weight on COMPOUND A NP properties.

TABLE 4

Properties of NP formulations for PK and PK/PD study.

| NP | COMPOUND Load | COMPOUND A counter-ion | Particle Size (polydispersity) | COMPOUND A concentration (mg/mL) | Total COMPOUND A (mg) |
|---|---|---|---|---|---|
| NP-B | 5.2% | None | 119 nm (0.22) | 5.0 | 10.0 |
| NP-F | 2.2% | Oleic acid | 85 nm (0.29) | 2.2 | 4.4 |
| NP-C | 5.9% | Oleic acid | 123 nm (0.18) | 5.8 | 11.6 |
| NP-D | 7.8% | Trifluoroacetate | 96 nm (0.18) | 7.8 | 15.5 |
| NP-E | 2.6% | Trifluoroacetate | 135 nm (0.13) | 2.5 | 5.0 |

Example 5: Maximum Tolerated Dose (MTD) Properties of Polymeric Nanoparticles Containing 8-[4-(1-amino-cyclobutyl)phenyl]-9-phenyl-2H-[1,2,4]-triazolo-[3,4-f][1,6]-naphthyridin-3-one NPs from Example 4 were prepared on a larger scale for MTD studies. The properties of these NP formulations are shown in Table 5.

TABLE 5

Properties of NP formulations for MTD study.

| NP | Load (% w/w) | Particle Size (nm) | MK2206 concentration (mg/mL) | Total MK2206 (mg) |
|---|---|---|---|---|
| NP-F2 | 2.9 | 97 | 2.9 | 119.3 |
| NP-C2 | 6.9 | 125 | 6.9 | 343.5 |
| NP-D2 | 6.6 | 95 | 8.2 | 410 |
| NP-E2 | 2.3 | 109 | 2.3 | 94.3 |

The MTD for free (i.e., non-encapsulated) COMPOUND A administered per os (p.o.) once per week was 480 mg/kg.

The maximum feasible doses (MFD) and half MFD for NP formulations are shown in Table 6.

TABLE 6

MFD in mice (in mg/kg).

| NP | Once per week (1× W) | Twice per week (2× W) | Thrice per week (3× W) |
|---|---|---|---|
| NP-C MFD | 57 | 114 | 171 |
| NP-C ½ MFD | 28.5 | 57 | 85.5 |
| NP-D MFD | 79 | 158 | 237 |
| NP-D ½ MFD | 39.5 | 79 | 118.5 |

Example 6: Efficacy of Polymeric Nanoparticles Containing 8-[4-(1-amino-cyclobutyl)phenyl]9-phenyl-2H-[1,2,4]-triazolo-[3,4-f][1,6]-naphthyridin-3-one Formulations NP-C and NP-D from Example 4 were selected for efficacy studies and were prepared along with placebo NPs containing no COMPOUND A. The properties of these NP formulations are shown in Table 7. These formulations were administered orally to SCID mice having VcaP prostate cancer xenografts.

TABLE 7

Properties for NP formulations for efficacy study.

| NP | Load (% w/w) | Particle Size (nm) | COMPOUND A concentration (mg/mL) | Total mL |
|---|---|---|---|---|
| NP-D3 | 7.9 | 106 | 7.9 | 210 |
| NP-C3 | 6.1 | 108 | 5.7 | 210 |
| Placebo | N/A | 91 | N/A | 112 |

Figure 5:
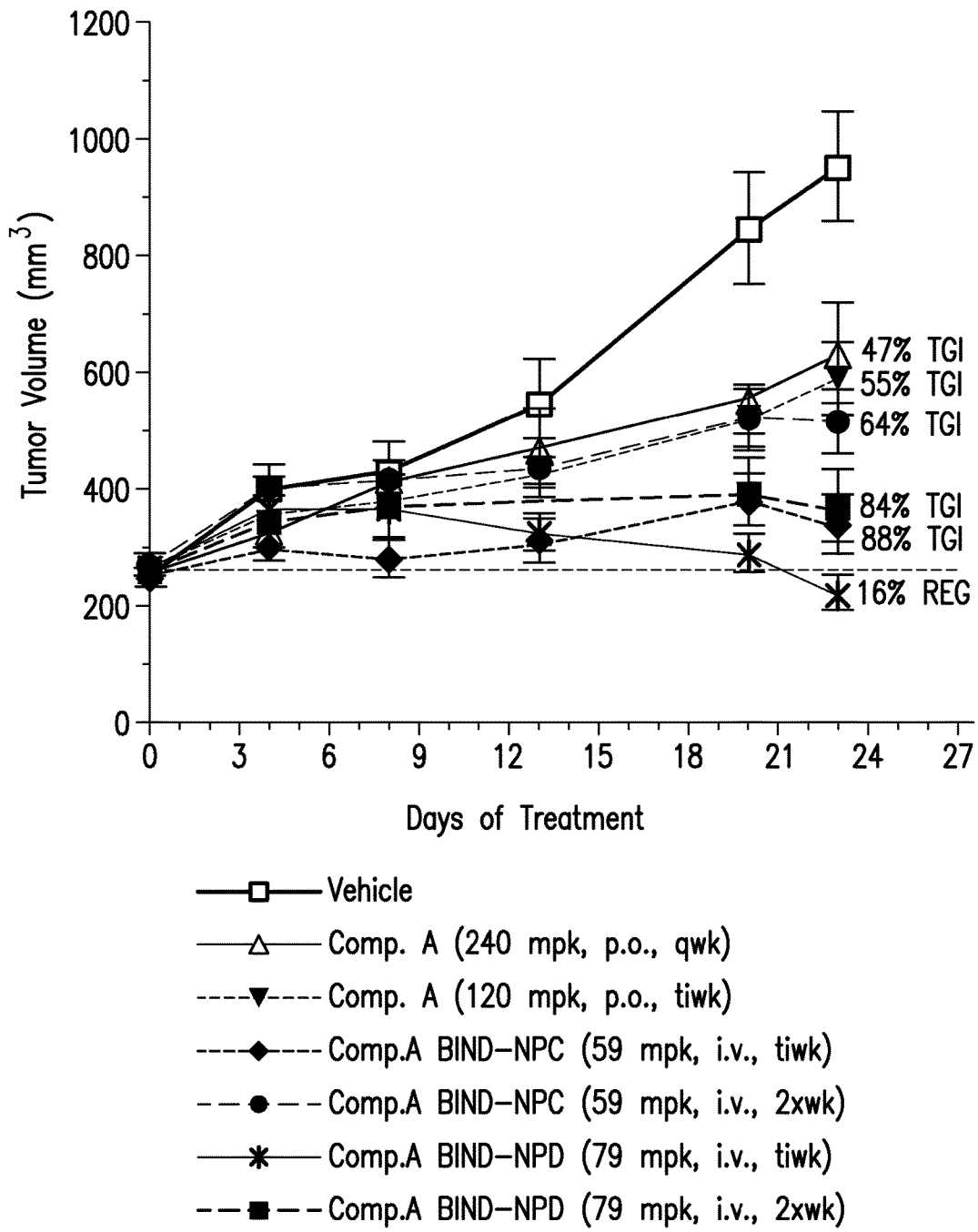
FIG. 5 shows tumor volume as a function of days of treatment for VCaP xenograft mice treated with free COMPOUND A versus COMPOUND A nanoparticles.

FIG. 5 shows dose-dependent tumor growth inhibition (TGI) & Tumor Regression Observed upon COMPOUND A Nanoparticle Treatment of mice having VCaP prostate cancer xenografts.

Figure 6:
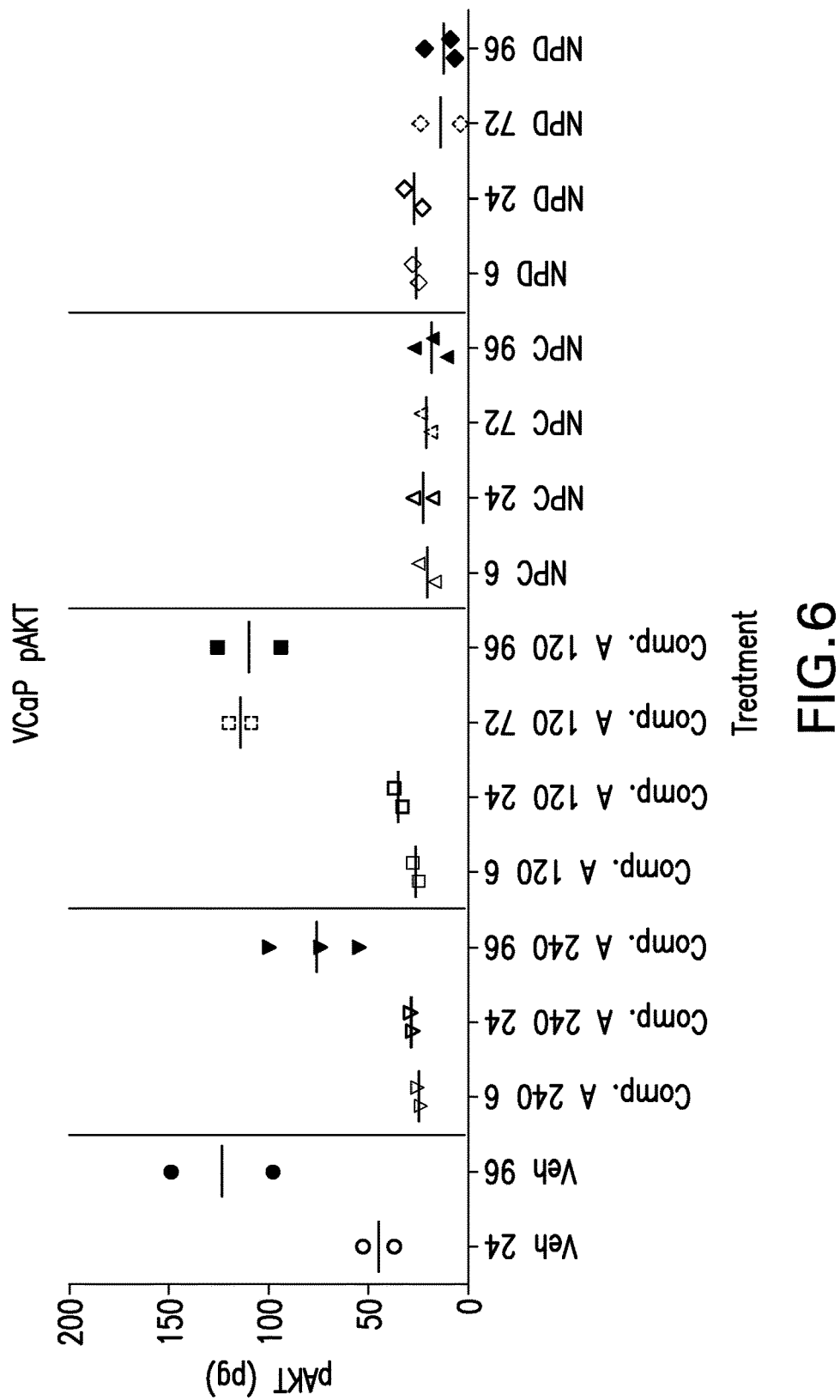
FIG. 6 shows Phospho-AKT (pAKT) levels 6 hours, 24 hours, 72 hours, or 96 hours after dosing VCaP xenograft mice with free COMPOUND A versus COMPOUND A nanoparticles.

FIG. 6 shows Phospho-AKT (pAKT) levels 6 hours, 24 hours, 72 hours, or 96 hours after dosing for NP-C & NP-D treatment groups ("NPC" and "NPD", respectively), free COMPOUND A ("COMPOUND A") groups, and vehicle only ("Veh") groups. The results show that pAKT levels are diminished for NPC and NPD groups as compared to free COMPOUND A or Veh groups.

Figure 7:
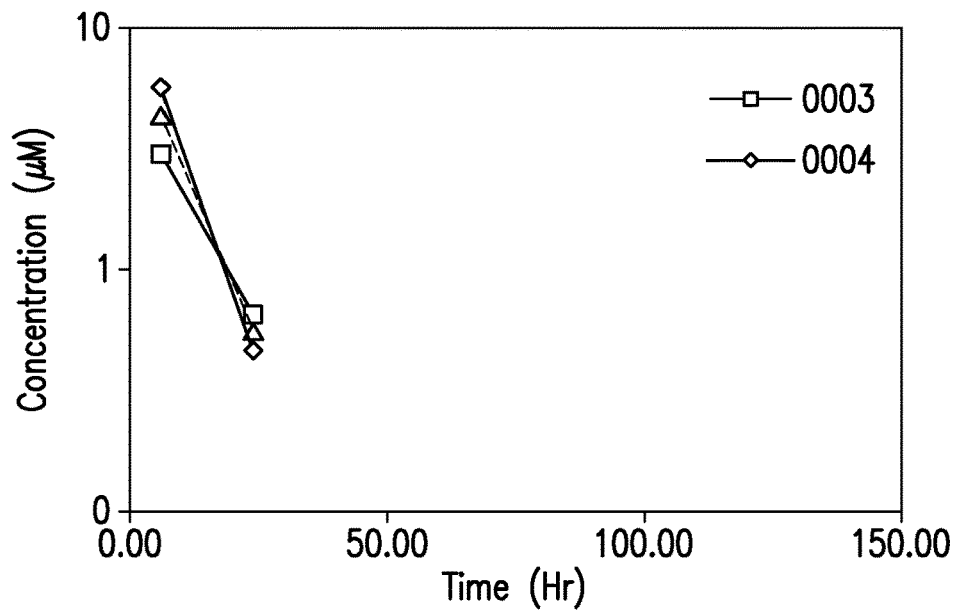
FIG. 7 shows the blood concentrations of COMPOUND A in mice dosed with free COMPOUND A (top panel) or COMPOUND A nanoparticles (bottom panel).
Figure 7:
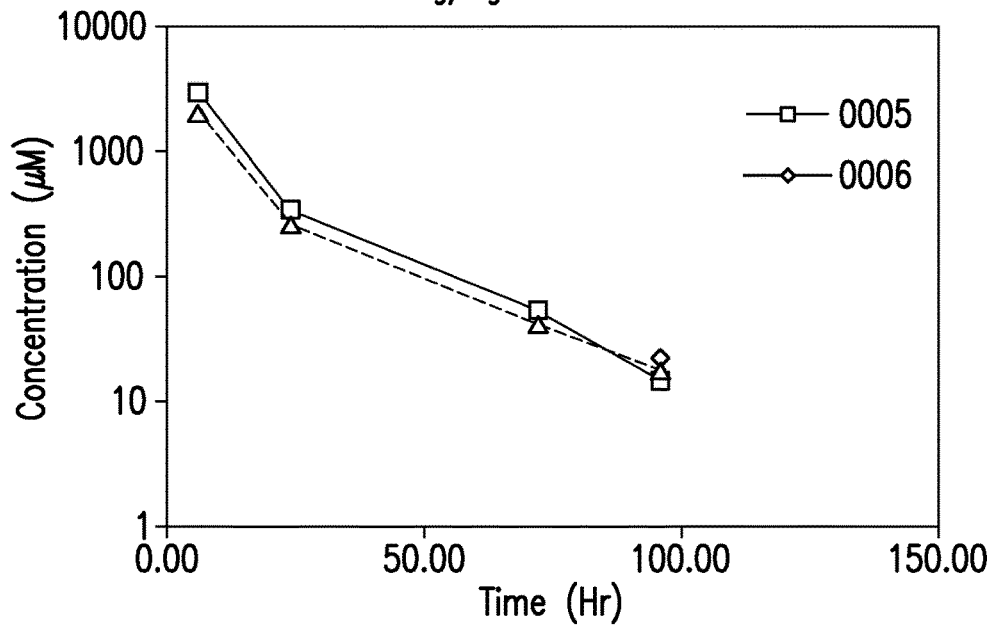

FIG. 7 shows the blood concentrations of COMPOUND A in mice dosed with free COMPOUND A (top panel) or NP-C formulation (bottom panel).

Figure 8:
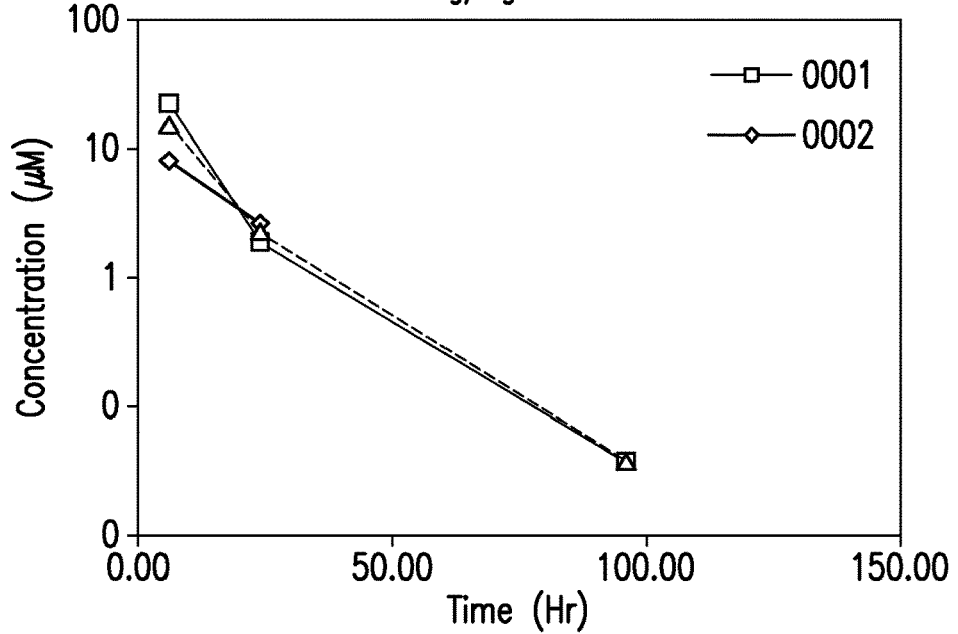
FIG. 8 shows the blood concentrations of COMPOUND A in mice dosed with free COMPOUND A (top panel) or COMPOUND A nanoparticles (bottom panel).
Figure 8:
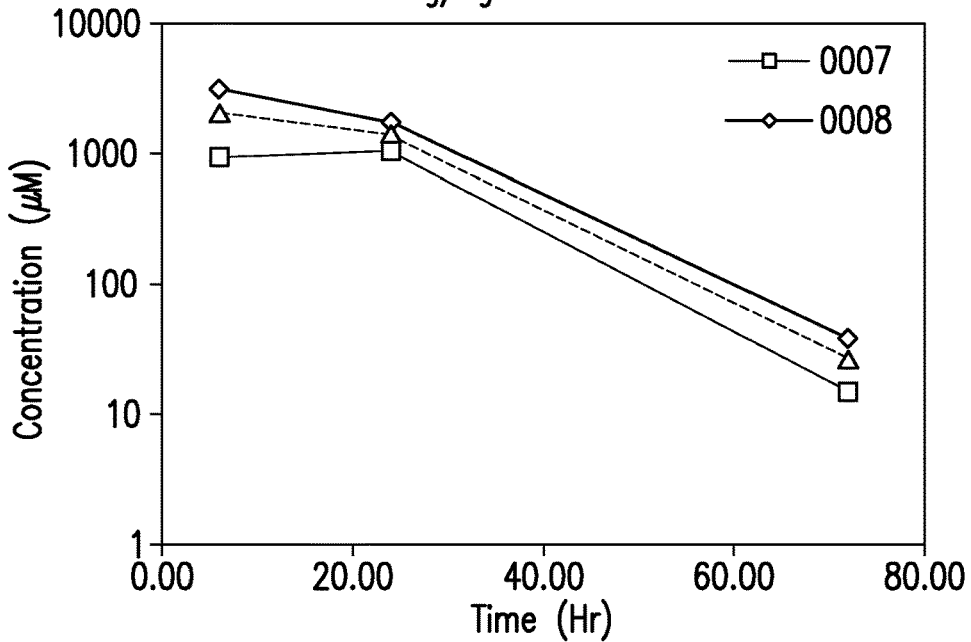

FIG. 8 shows the blood concentrations of COMPOUND A in mice dosed with free COMPOUND A (top panel) or NP-D formulation (bottom panel).

Figure 9:
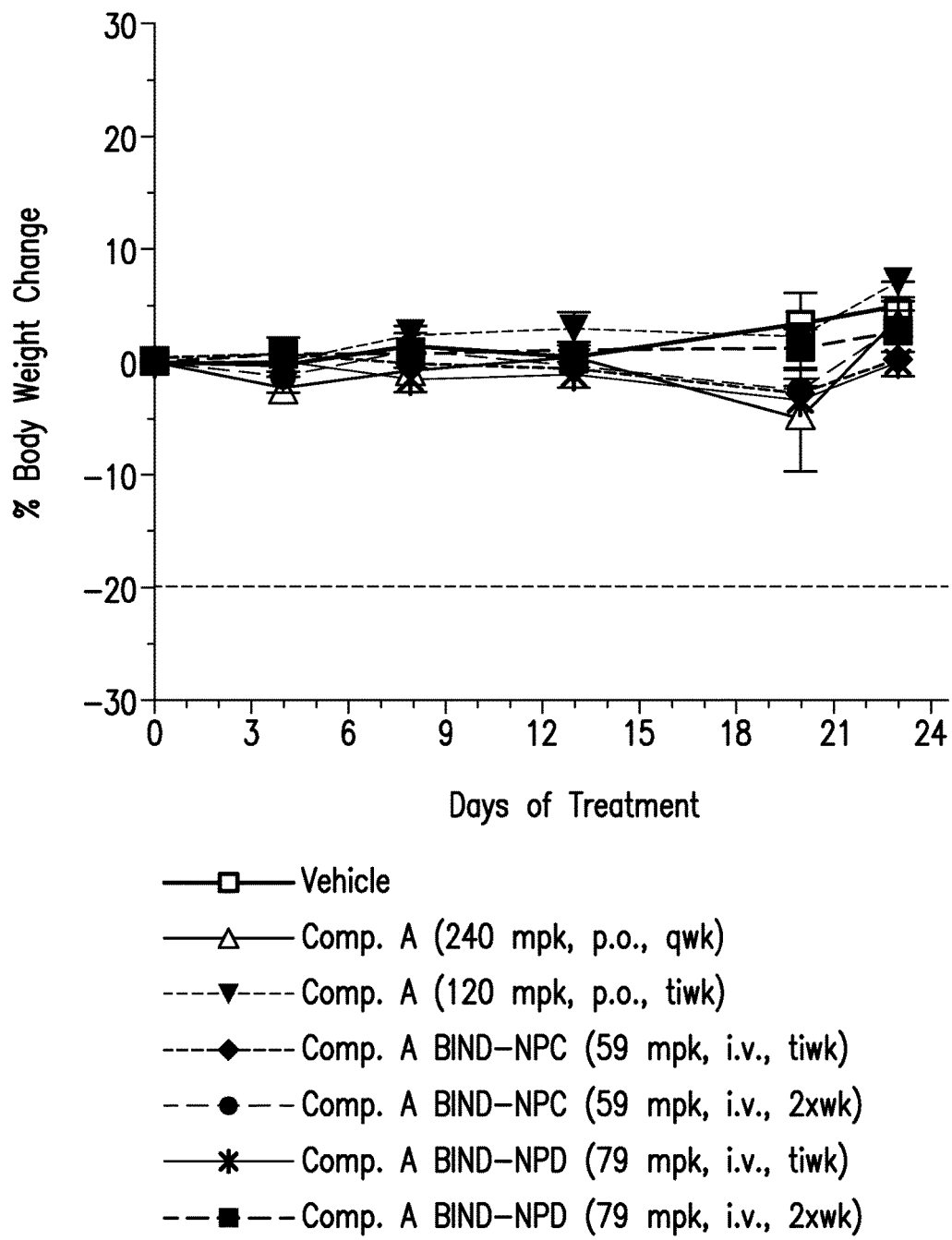
FIG. 9 shows percent body weight change as a function of days in VcaP prostate cancer xenograft mice treated with vehicle, free COMPOUND A, or COMPOUND A nanoparticles.

FIG. 9 shows the percent body weight change as a function of days in VcaP prostate cancer xenograft mice treated with vehicle, free COMPOUND A, NP-C, or NP-D.

Figure 10:
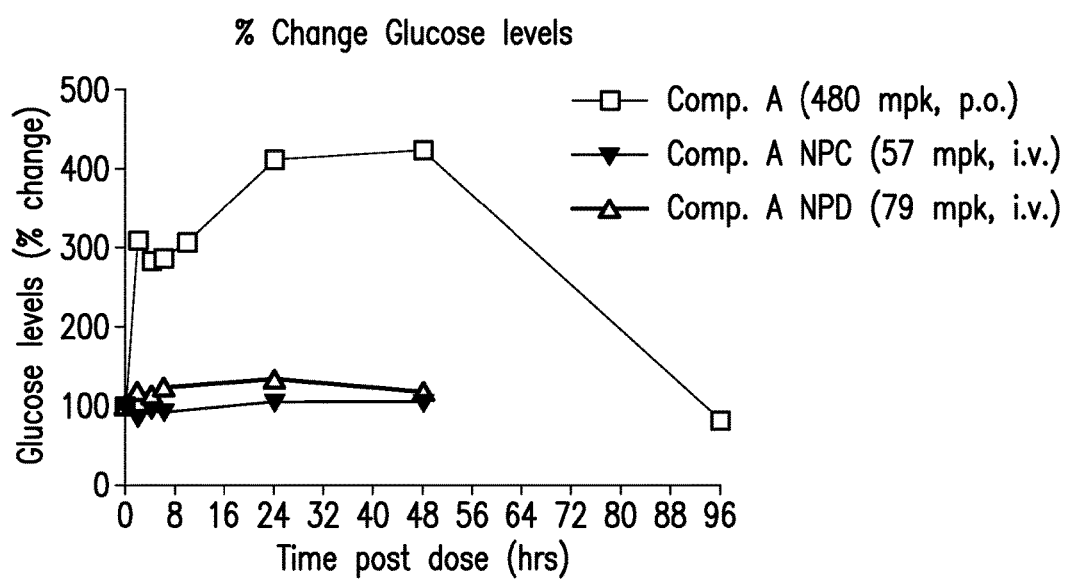
FIG. 10 shows blood glucose levels as a function of time post dose for VCaP xenograft mice treated with free COMPOUND A or COMPOUND A nanoparticles.

FIG. 10 shows that non-tumor bearing SCID mice display hyperglycemia following acute treatment with oral COMPOUND A but not with NP-C or NP-D.

Figure 11:
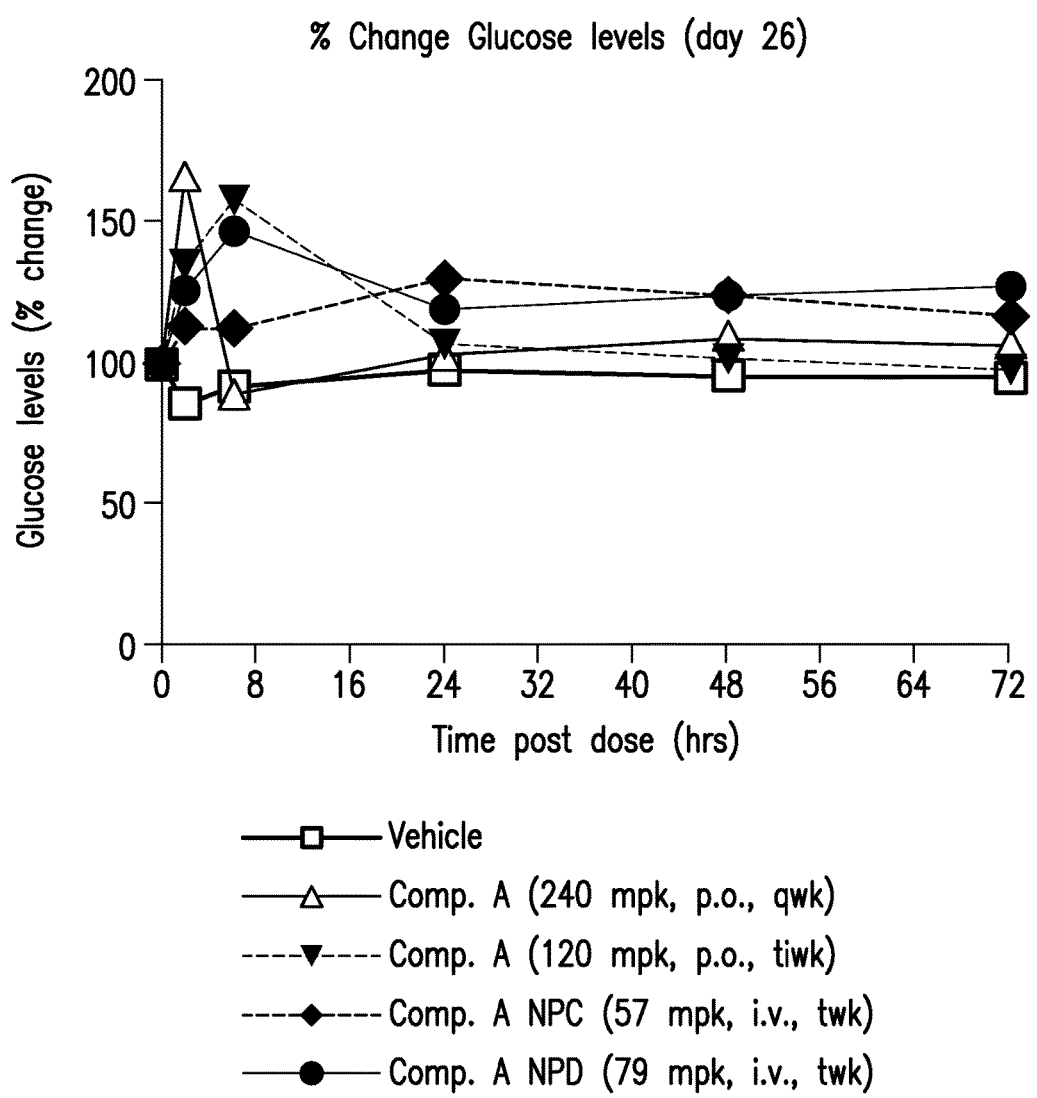
FIG. 11 shows blood glucose levels as a function of time post dose for VCaP xenograft mice treated with free COMPOUND A or COMPOUND A nanoparticles.

FIG. 11 shows that blood glucose levels in VCaP xenograft mice normalize by the end of the study for each treatment group.

Figure 12:
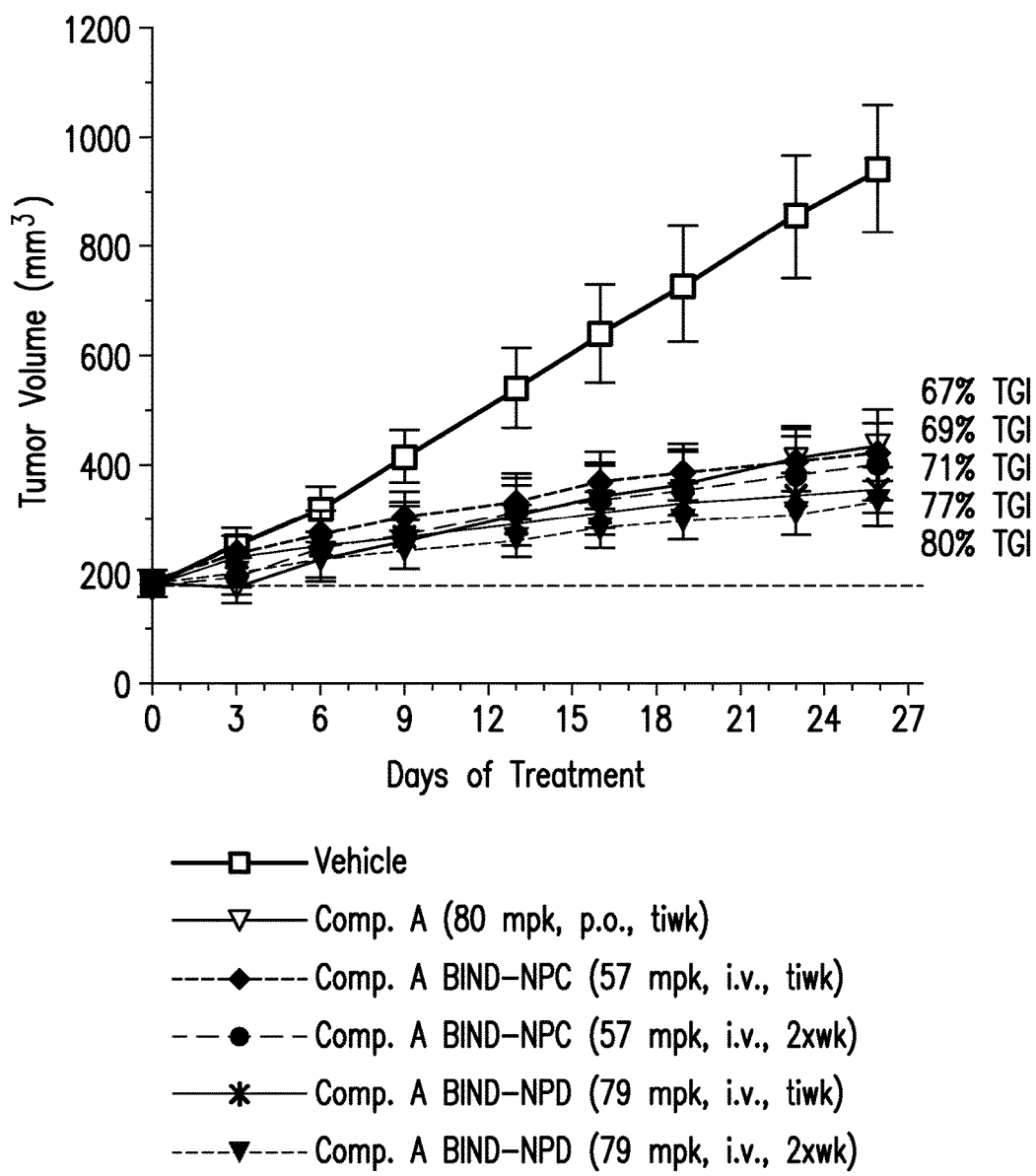
FIG. 12 shows tumor volume as a function of days of treatment for BT-474 xenograft mice treated with free COMPOUND A versus COMPOUND A nanoparticles.

FIG. 12 shows dose-dependent tumor growth inhibition (TGI) of BT-474 breast cancer xenografts in mice upon COMPOUND A Nanoparticle Treatment.

Figure 13:
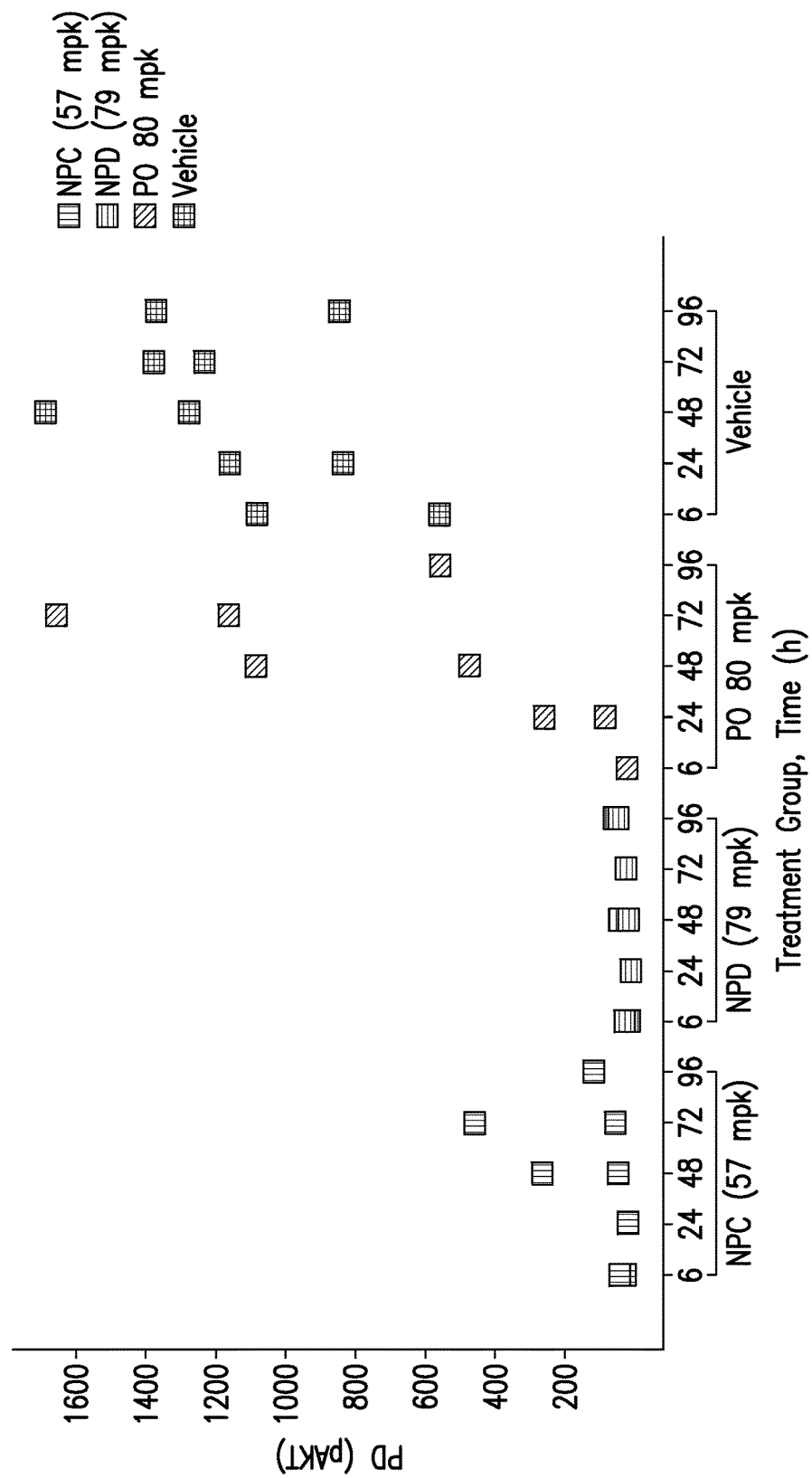
FIG. 13 shows Phospho-AKT (pAKT) levels 6 hours, 24 hours, 48 hours, 72 hours, or 96 hours after dosing BT-474 xenograft mice with free COMPOUND A versus COMPOUND A nanoparticles.

FIG. 13 shows Phospho-AKT (pAKT) levels 6 hours, 24 hours, 48 hours, 72 hours, or 96 hours after dosing for NP-C & NP-D treatment groups ("NPC" and "NPD", respectively), free COMPOUND A ("PO 80 mpk") groups, and vehicle only ("Vehicle") groups for BT-474 breast cancer xenograft mice. The results show that pAKT levels are diminished for NPC and NPD groups as compared to free COMPOUND A or Vehicle groups.

Figure 14:
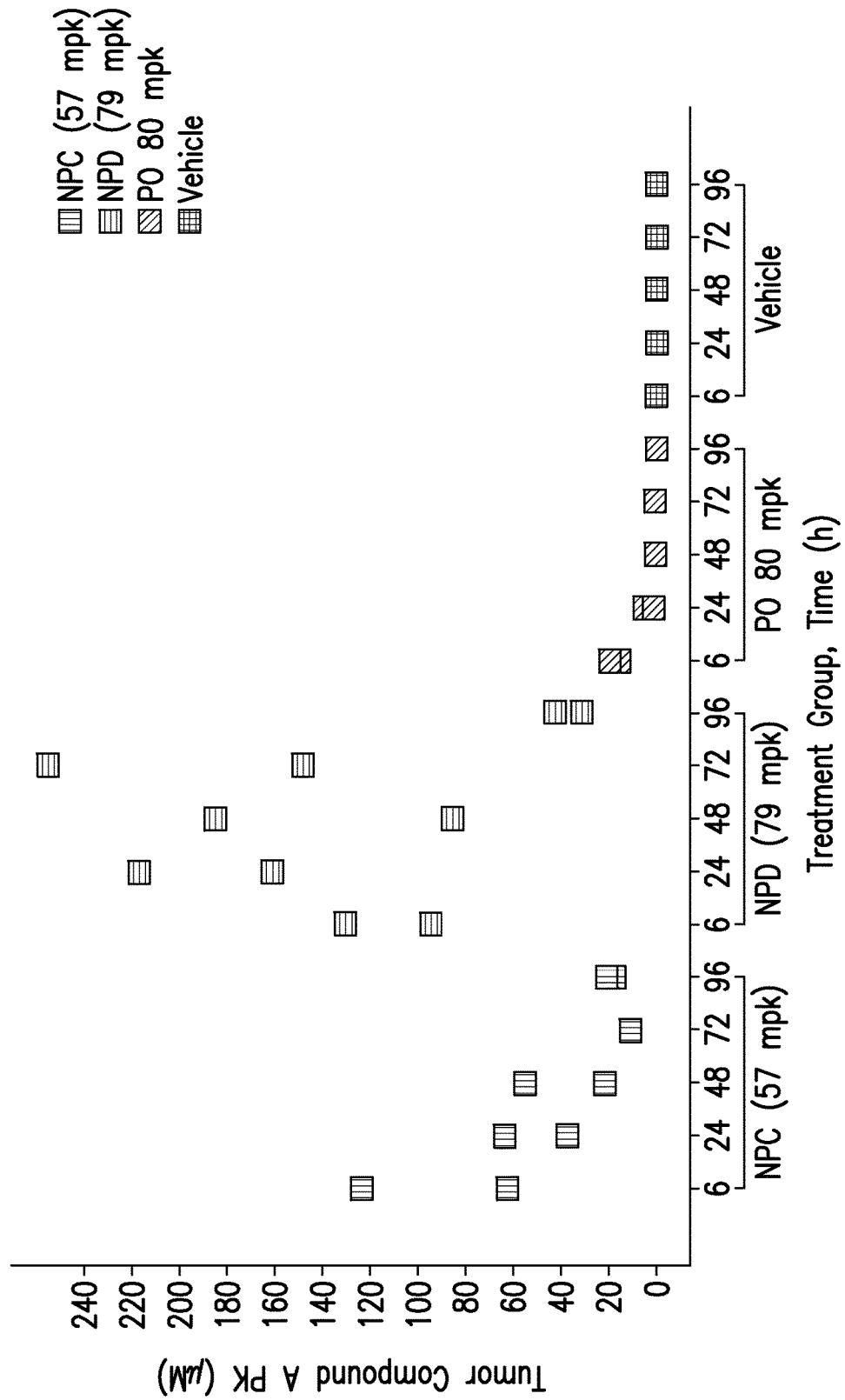
FIG. 14 shows tumor levels of COMPOUND A in BT-474 breast cancer xenograft mice at 6 hours, 24 hours, 48 hours, 72 hours, or 96 hours after dosing with free COMPOUND A or COMPOUND A nanoparticles.

FIG. 14 shows pharmacokinetic results 6 hours, 24 hours, 48 hours, 72 hours, or 96 hours after dosing for NP-C & NP-D treatment groups ("NPC" and "NPD", respectively), free COMPOUND A ("PO 80 mpk") groups, and vehicle only ("Vehicle") groups for BT-474 breast cancer xenograft mice. The results show that tumor levels of COMPOUND A were much higher for NPC and NPD groups as compared to free COMPOUND A or Vehicle groups.

Figure 15:
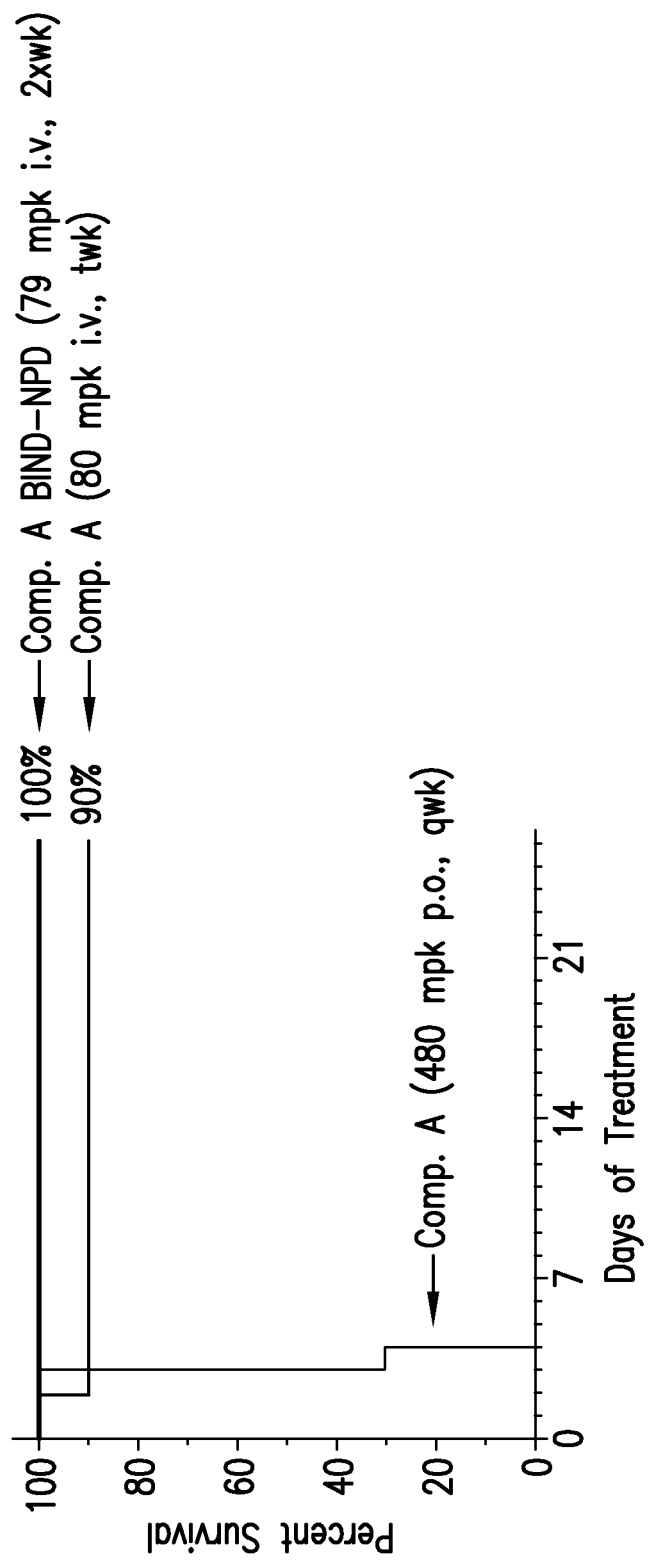
FIG. 15 shows percent survival of BT-474 xenograft mice as a function of days of treatment with free COMPOUND A versus COMPOUND A nanoparticles.

FIG. 15 shows MTD dosing for NP-D could not be achieved with BT-474 xenografts in SCID mice, whereas free COMPOUND A exhibited toxicity.

Figure 16:
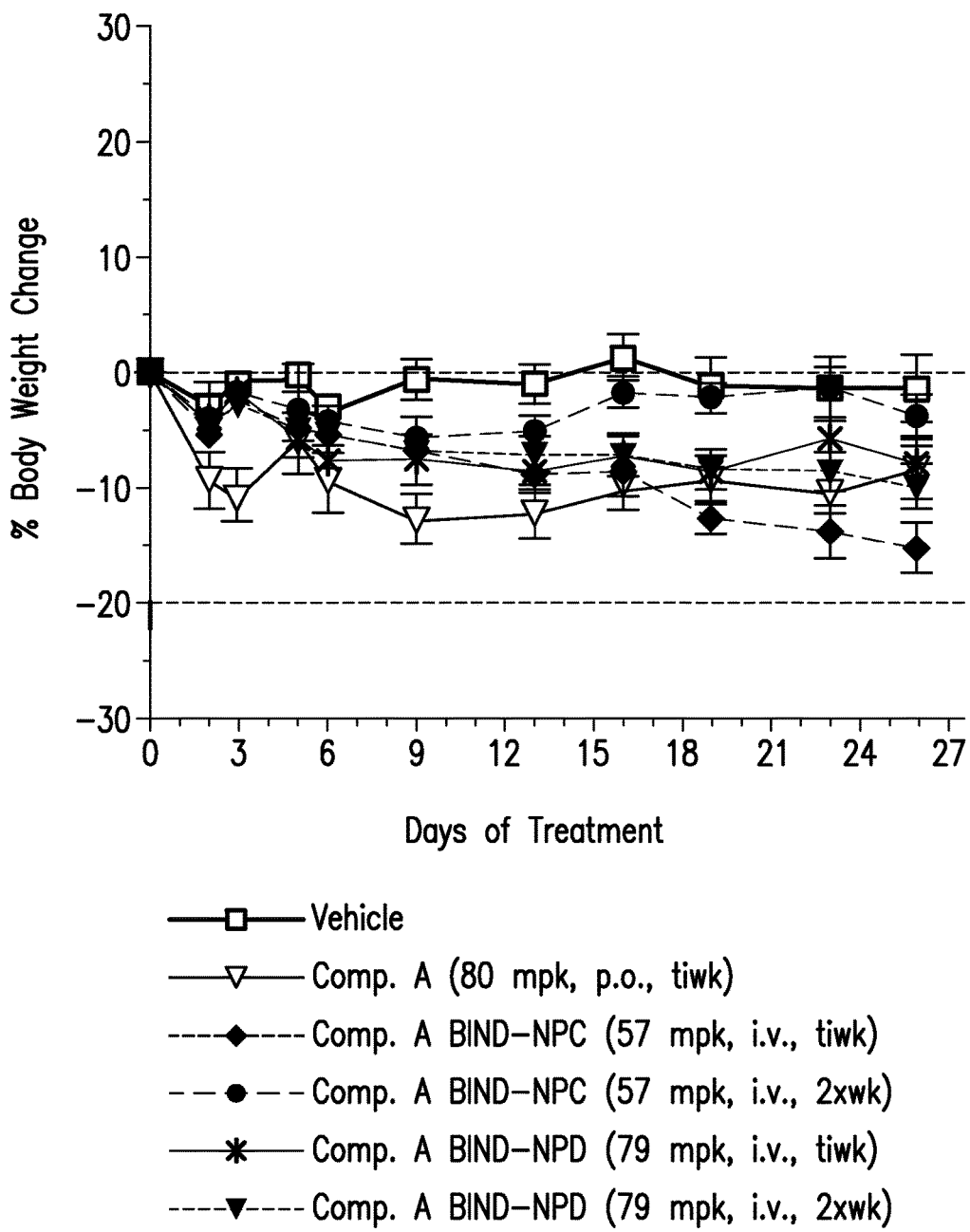
FIG. 16 shows percent body weight change as a function of days in BT-474 breast cancer xenograft mice treated with vehicle, free COMPOUND A, or COMPOUND A nanoparticles.

FIG. 16 shows the percent body weight change as a function of days in BT-474 breast cancer xenograft mice treated with vehicle, free COMPOUND A, NP-C, or NP-D.

Figure 17:
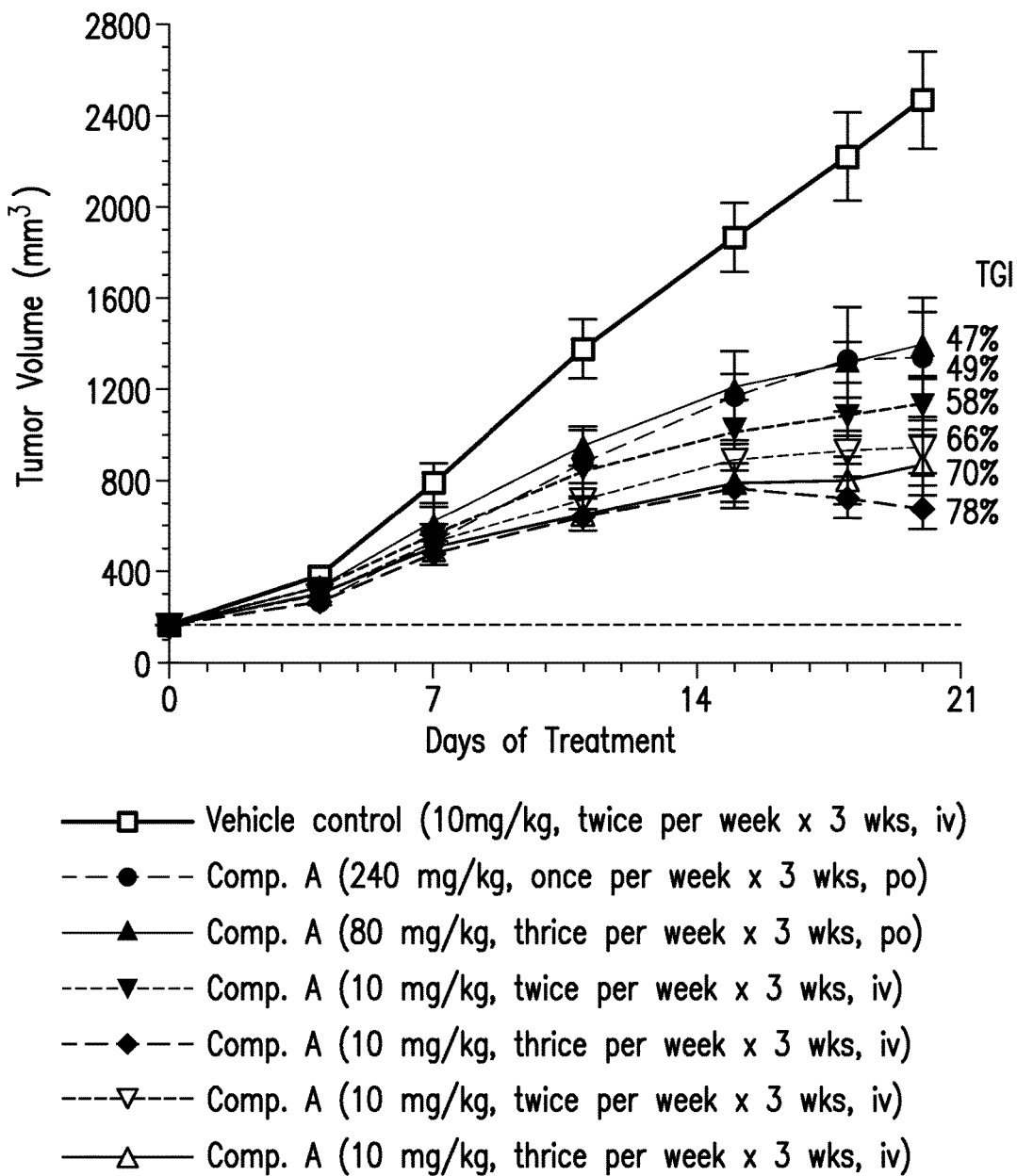
FIG. 17 shows tumor volume as a function of days of treatment for SKOV3 xenograft mice treated with free COMPOUND A versus COMPOUND A nanoparticles.

FIG. 17 shows dose-dependent tumor growth inhibition (TGI) of SKOV3 ovarian cancer xenografts in mice upon COMPOUND A Nanoparticle Treatment (COMPOUND AC (i.e., NP-C) and COMPOUND AD (i.e., NP-D)).

Figure 18:
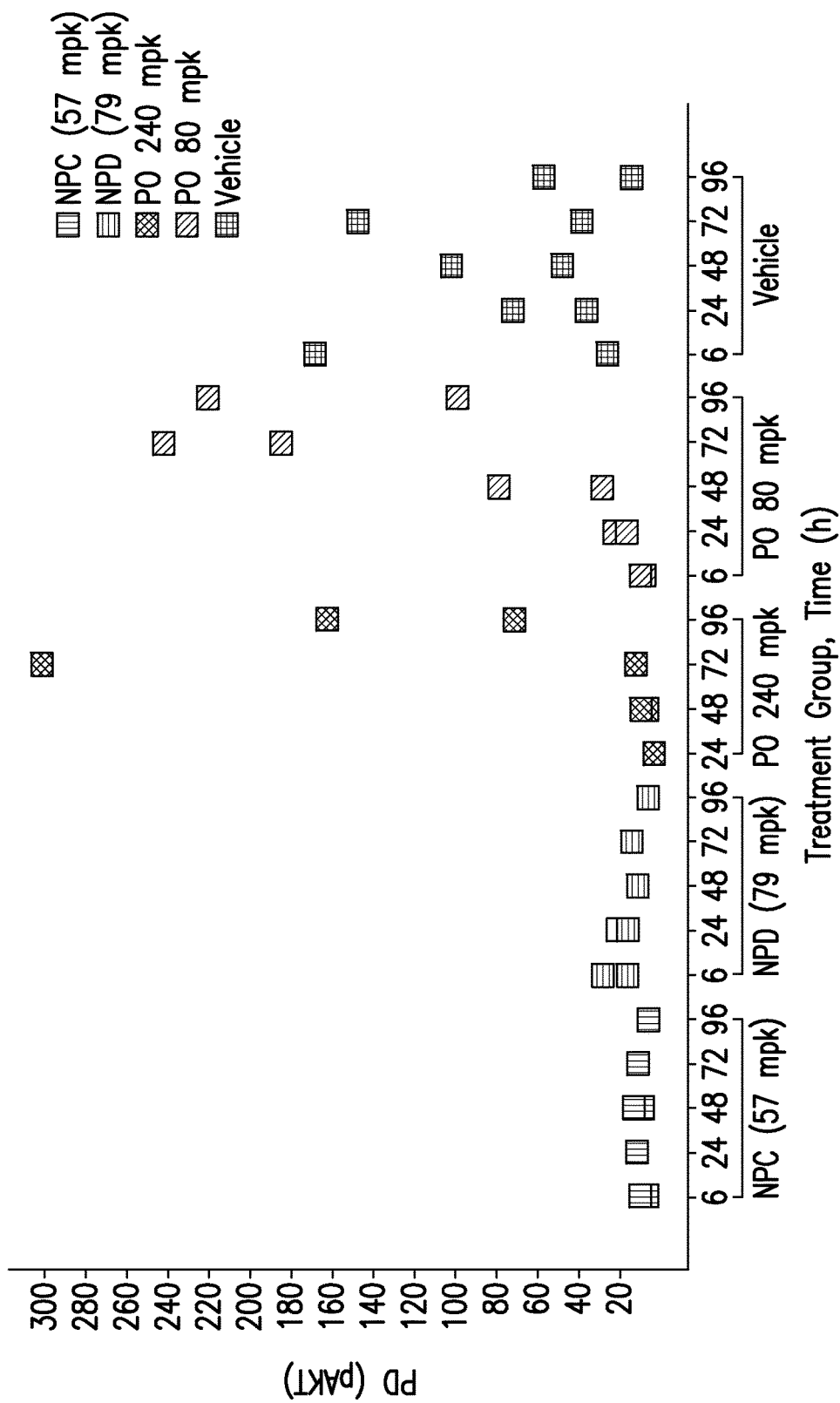
FIG. 18 shows Phospho-AKT (pAKT) levels 6 hours, 24 hours, 48 hours, 72 hours, or 96 hours after dosing SKOV3 xenograft mice with free COMPOUND A versus COMPOUND A nanoparticles.

FIG. 18 shows Phospho-AKT (pAKT) levels 6 hours, 24 hours, 48 hours, 72 hours, or 96 hours after dosing for NP-C & NP-D treatment groups ("NPC" and "NPD", respectively), free COMPOUND A ("PO 80 mpk") groups, and vehicle only ("Vehicle") groups for SKOV3 ovarian cancer xenograft mice. The results show that pAKT levels are diminished for NPC and NPD groups as compared to free COMPOUND A or Vehicle groups.

Figure 19:
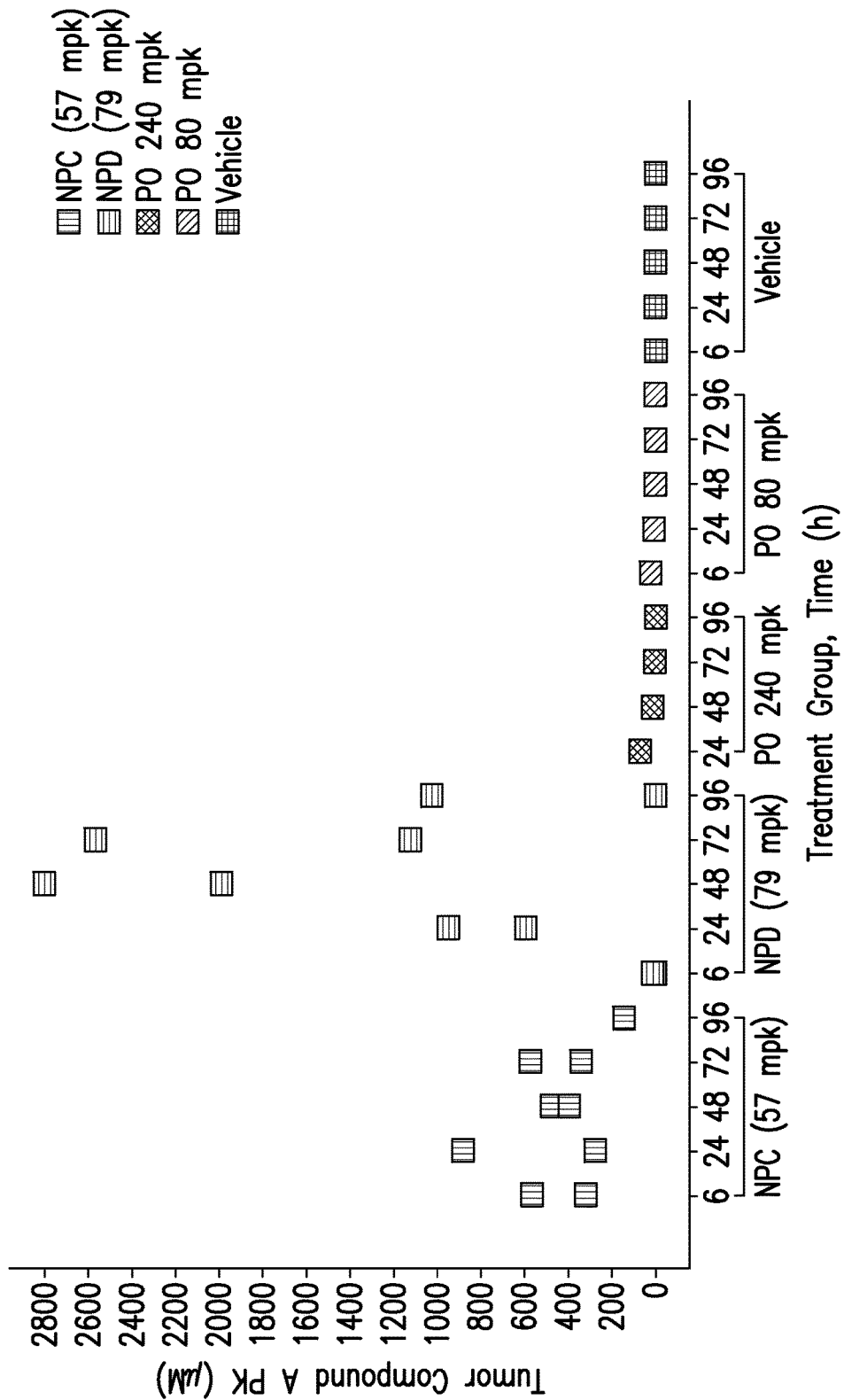
FIG. 19 shows tumor levels of COMPOUND A in SKOV3 breast cancer xenograft mice at 6 hours, 24 hours, 48 hours, 72 hours, or 96 hours after dosing with free COMPOUND A or COMPOUND A nanoparticles.
Figure 20:
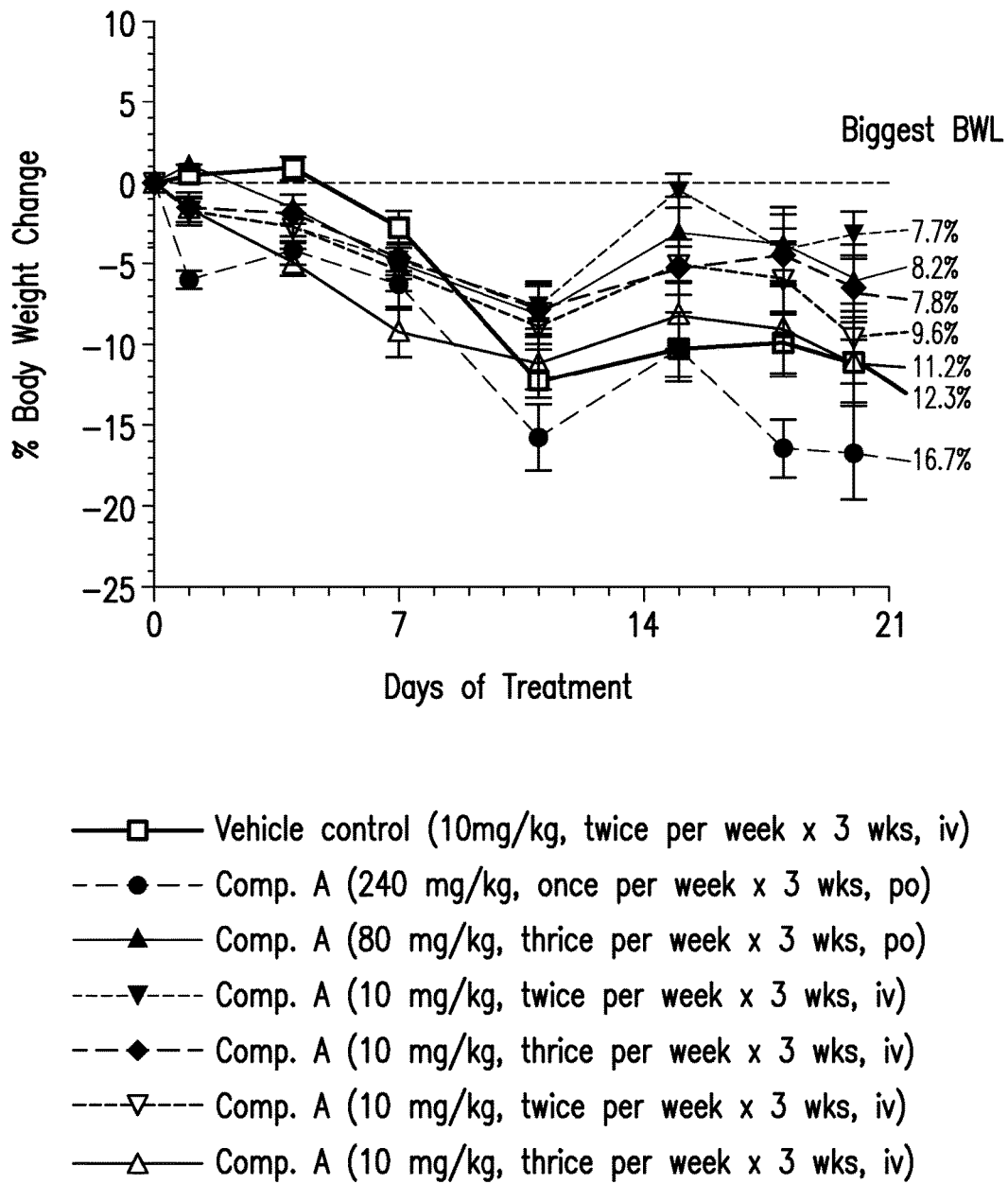
FIG. 20 shows percent body weight change as a function of days in SKOV3 breast cancer xenograft mice treated with vehicle, free COMPOUND A, or COMPOUND A nanoparticles.

FIG. 19 shows pharmacokinetic results 6 hours, 24 hours, 48 hours, 72 hours, or 96 hours after dosing for NP-C & NP-D treatment groups ("NPC" and "NPD", respectively), free COMPOUND A ("PO 80 mpk") groups, and vehicle only ("Vehicle") groups for SKOV3 ovarian cancer xenograft mice. The results show that tumor levels of COMPOUND A were much higher for NPC and NPD groups as compared to free COMPOUND A or Vehicle groups. FIG. 20 shows the percent body weight change as a function of days in SKOV3 ovarian cancer xenograft mice treated with vehicle, free COMPOUND A, NP-C, or NP-D.

EQUIVALENTS

Those skilled in the art will recognize, or be able to ascertain using no more than routine experimentation, many equivalents to the specific embodiments of the invention described herein. Such equivalents are intended to be encompassed by the following claims.

INCORPORATION BY REFERENCE

The entire contents of all patents, published patent applications, websites, and other references cited herein are hereby expressly incorporated herein in their entireties by reference.

What is claimed is:

1. A polymeric nanoparticle comprising:
   about 50 to about 99.8 weight percent of a diblock poly(lactic) acid-poly(ethylene)glycol copolymer or a diblock poly(lactic acid-co-glycolic acid)-poly(ethylene)glycol copolymer; wherein the total amount of poly(ethylene)glycol in the nanoparticle is about 10 to about 30 weight percent poly(ethylene)glycol; and
   about 0.2 to about 30 weight percent of a compound that is COMPOUND A represented by the formula:

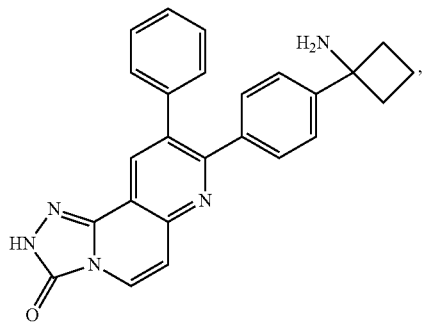 [SMILES: NC1(c2ccc(-c3nc4ccn5c(=O)[nH]nc5c4cc3-c3ccccc3)cc2)CCC1]

or a pharmaceutically acceptable salt thereof.

2. The nanoparticle of claim 1, wherein the poly(lactic) acid-poly(ethylene)glycol copolymer has a poly(lactic) acid number average molecular weight fraction of about 0.7 to about 0.9.

3. The nanoparticle of claim 1, wherein the nanoparticle comprises about 10 to about 25 weight percent poly(ethylene)glycol.

4. The nanoparticle of claim 1, wherein the poly(lactic) acid-poly(ethylene)glycol copolymer has a number average molecular weight of about 15 kDa to about 20 kDa poly (lactic acid) and a number average molecular weight of about 4 kDa to about 6 kDa poly(ethylene)glycol.

5. The nanoparticle of claim 1, comprising about 65 weight percent to about 85 weight percent of the copolymer.

6. The nanoparticle of claim 1, further comprising a substantially hydrophobic acid selected from the group consisting of cholic acid and oleic acid.

7. The nanoparticle of claim 1, further comprising about 5 to about 15 weight percent of a substantially hydrophobic acid selected from the group consisting of cholic acid and oleic acid.

8. The nanoparticle of claim 6, wherein the molar ratio of the substantially hydrophobic acid to the compound is about 0.9:1 to about 1.1:1, wherein the acid is cholic acid or oleic acid.

9. The nanoparticle of claim 6, wherein a $pK_a$ of the compound is at least about 1.0 $pK_a$ unit greater than a $pK_a$ of the hydrophobic acid.

10. The nanoparticle of claim 6, wherein the substantially hydrophobic acid and the compound form a hydrophobic ion pair in the nanoparticle.

11. The nanoparticle of claim 1, comprising about 5 to about 20 weight percent of the compound.

12. A nanoparticle comprising:
   about 50 to about 97.95 weight percent of a diblock poly(lactic) acid-poly(ethylene)glycol copolymer, wherein the total amount of poly(ethylene)glycol in the nanoparticle is about 10 to about 30 weight percent poly(ethylene)glycol;
   about 0.05 to about 35 weight percent of a substantially hydrophobic acid selected from the group consisting of cholic acid and oleic acid; and
   about 2 to about 30 weight percent of a compound that is COMPOUND A represented by the formula:

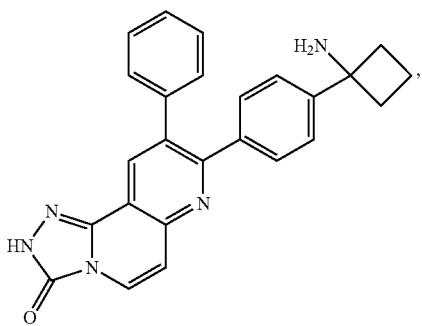 [SMILES: NC1(c2ccc(-c3nc4ccn5c(=O)[nH]nc5c4cc3-c3ccccc3)cc2)CCC1]

or a pharmaceutically acceptable salt thereof.

13. The nanoparticle of claim 12, wherein the poly(lactic) acid-poly(ethylene)glycol copolymer has a poly(lactic) acid number average molecular weight fraction of about 0.7 to about 0.9.

14. The nanoparticle of claim 12, wherein the nanoparticle comprises about 10 to about 25 weight percent poly(ethylene)glycol.

15. The nanoparticle of claim 12, wherein the poly(lactic) acid-poly(ethylene)glycol copolymer has a number average molecular weight of about 15 kDa to about 20 kDa poly(lactic acid) and a number average molecular weight of about 4 kDa to about 6 kDa poly(ethylene)glycol.

16. The nanoparticle of claim 12, comprising about 65 weight percent to about 85 weight percent of the copolymer.

17. A pharmaceutically acceptable composition comprising a plurality of polymeric nanoparticles of claim 1 and a pharmaceutically acceptable excipient.

18. A method of treating cancer in a patient in need thereof, comprising administering to the patient a therapeutically effective amount of a composition comprising the polymeric nanoparticle of claim 1.

19. The method of claim 18, wherein the cancer is prostate cancer.

20. The method of claim 18, wherein the cancer is breast cancer or ovarian cancer.

* * * * *

UNITED STATES PATENT AND TRADEMARK OFFICE
CERTIFICATE OF CORRECTION

PATENT NO. : 10,022,360 B2  
APPLICATION NO. : 15/126894  
DATED : July 17, 2018  
INVENTOR(S) : Young Ho Song et al.

Page 1 of 1

It is certified that error appears in the above-identified patent and that said Letters Patent is hereby corrected as shown below:

On the Title Page

At Item (71), delete:
"Merck Sharp & Dohme Corp., Rahway, NJ (US); BIND Therapeutics, Inc., Cambridge, MA (US)"

Add:
-- Merck Sharp & Dohme Corp., Rahway, NJ (US); Pfizer Inc., New York, NY (US) --

Signed and Sealed this
Twenty-seventh Day of November, 2018

Andrei Iancu
*Director of the United States Patent and Trademark Office*